(12) United States Patent
Griffin et al.

(10) Patent No.: US 7,973,031 B2
(45) Date of Patent: Jul. 5, 2011

(54) STAUROSPORINE DERIVATIVES AS INHIBITORS OF FLT3 RECEPTOR TYROSINE KINASE ACTIVITY

(75) Inventors: James Douglas Griffin, Brookline, MA (US); Paul William Manley, Arlesheim (CH)

(73) Assignees: Novartis AG, Basel (CH); Dana-Farber Cancer Institute Inc, Boston, MA (US)

( * ) Notice: Subject to any disclaimer, the term of this patent is extended or adjusted under 35 U.S.C. 154(b) by 719 days.

(21) Appl. No.: 10/493,786

(22) PCT Filed: Oct. 29, 2002

(86) PCT No.: PCT/EP02/12076
§ 371 (c)(1),
(2), (4) Date: Sep. 15, 2004

(87) PCT Pub. No.: WO03/037347
PCT Pub. Date: May 8, 2003

(65) Prior Publication Data
US 2005/0020570 A1    Jan. 27, 2005

Related U.S. Application Data

(60) Provisional application No. 60/339,031, filed on Oct. 30, 2001, provisional application No. 60/338,185, filed on Dec. 7, 2001.

(51) Int. Cl.
*A61P 35/02* (2006.01)
*A61K 31/55* (2006.01)
*A61K 31/535* (2006.01)
*C07D 498/22* (2006.01)
*C07D 487/04* (2006.01)
*C07D 487/14* (2006.01)
*C07D 519/00* (2006.01)

(52) U.S. Cl. .................. 514/211.08; 540/545
(58) Field of Classification Search ............. 514/211.08; 540/545
See application file for complete search history.

(56) References Cited

U.S. PATENT DOCUMENTS

| | | | |
|---|---|---|---|
| 5,093,330 A | 3/1992 | Caravatti et al. | |
| 5,545,636 A | 8/1996 | Heath, Jr. et al. | |
| 5,658,898 A | 8/1997 | Weder et al. | |
| 5,726,164 A | 3/1998 | Weder et al. | |

FOREIGN PATENT DOCUMENTS

| | | |
|---|---|---|
| EP | 0 296 110 | 12/1988 |
| EP | 0 383 919 | 8/1990 |
| EP | 0 397 060 | 11/1990 |
| EP | 0 575 955 | 12/1993 |
| EP | 0 624 586 | 11/1994 |
| EP | 0 711 556 | 5/1996 |
| EP | 0 711 557 | 5/1996 |
| EP | 0 733 358 | 9/1996 |
| EP | 0 733 372 | 9/1996 |
| EP | 0 990 442 | 4/2000 |
| EP | 1 109 020 | 6/2001 |
| HU | 225297 | 9/2006 |
| WO | 91 09034 | 6/1991 |
| WO | WO 93/07153 | 4/1993 |
| WO | WO 9402486 | 3/1994 |
| WO | WO 95/32976 | 12/1995 |
| WO | WO 98/07415 | 2/1998 |
| WO | 99 02532 | 1/1999 |
| WO | WO 00/48571 | 8/2000 |

OTHER PUBLICATIONS

Sedlak et al., Protein Kinase Inhibitor-Induced Alterations of Drug Uptake, Cell Cycle and Surface Antigen Expression in Human Multidrug-Resistant (Pgp and MRP) Promyelocytic Leukemia HL-60 Cells, Leukemia Research, vol. 21, No. 5, pp. 449-458, 1997.*
Millward et al., The Multikinase inhibitor midostaurin (PKC412A) Lacks Activity in Metastatic Melanoma: A Phase IIA Clinical and Biologic Study, British Journal of Cancer, vol. 95, pp. 829-834, 2006.*
Heidel et al., Clinical Resistance to the Kinase Inhibitor PKC412 in Acute Myeloid Leukemia by Mutation of Asn-676 in the FLT3 Tyrosine Kinase Domain, Blood, vol. 107, No. 1, pp. 293-300, Jan. 1, 2006.*
Weisberg et al., Inhibition of Mutant FLT3 Receptors in Leukemia Cells by the Small Molecule Tyrosine Kinase Inhibitor PKC412, Cancer Cell, vol. 1, No. 3, Apr. 2002, pp. 433-443.*
Meyer et al., "A derivative of Staurosporine (CGP 41 251) shows selectively for protein kinase C inhibition and in vitro anti-proliferative as well as in vito anti-tumor activity", Int. J. Cancer, vol. 43, 851-856, 1989 pp. 851, 854 and 855.
Fallon, "Staurosporine inhibits a tyrosine protein kinase in human hepatoma cell membrances," Biochem, Biophys. Res. Commun., vol. 170, No. 3, 1191-1196, 1990.
Secrist et al, "Preferential inhibition of the platelet-derived growth factor receptor tyrosine kinase by staurosporine", J. Biol. Chem., vol. 265, No. 33, 20394-20400, 1990.
Meshinchi, et al., "Prevalence and prognostic significance of Flt3 internal tandem duplication in pediatric acute myeloid leukemia", Blood, vol. 97, No. 1, 89-94, 2001.
Lisovsky et al, "Flt3 ligand stimulates proliferation and inhibits apoptosis of acute myeloid leukemia cells: regulation of Bcl-2 and Bax", Blood, vol. 88, No. 10, 3987-3997, 1996.
Grosis, Konstantina, "Midostaurin Novartis AG", Curr. Opin. Oncol. Endocr. Metab. Inves., (2002), vol. 2, pp. 92-103.

\* cited by examiner

*Primary Examiner* — Brenda Coleman
(74) *Attorney, Agent, or Firm* — George R. Dohmann; Kristin E. Konzak; Lydia T. McNally

(57) ABSTRACT

The present invention relates to the use of staurosporines derivatives for the preparation of a drug for the treatment of diseases involving deregulated FLT3 receptor tyrosine kinase activity, especially for the curative and/or prophylactic treatment of leukemias and myelodysplastic syndromes, and to a method of treating diseases involving deregulated FLT3 receptor tyrosine kinase activity.

6 Claims, No Drawings

STAUROSPORINE DERIVATIVES AS INHIBITORS OF FLT3 RECEPTOR TYROSINE KINASE ACTIVITY

This application is a national stage entry under 35 USC §371 of PCT/EP02/12076, filed Oct. 29, 2002, which claims benefit of Provisional Application No. 60/339,031 filed Oct. 30, 2001, and Provisional Application No. 60/338,185 filed Dec. 7, 2001, each of which is here incorporated by reference in its entirety.

The present invention relates to the use of staurosporine derivatives of formula A, B, C, D, I, II, III, IV, V, VI and VII: (hereinafter. "STAUROSPORINE DERIVATIVES") for the preparation of a drug for the treatment of diseases involving deregulated FLT3 receptor tyrosine kinase activity, especially for the curative and/or prophylactic treatment of leukemias and myelodysplastic syndromes, and to a method of treating diseases involving deregulated FLT3 receptor tyrosine kinase activity.

The invention relates to the use of staurosporine derivatives of formula,

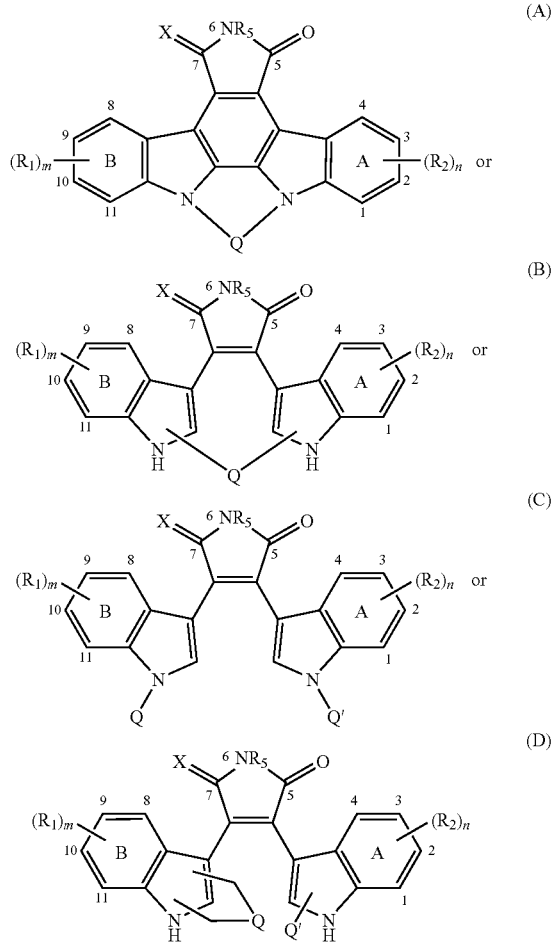

wherein $R_1$, and $R_2$ are, independently of one another, unsubstituted or substituted alkyl, hydrogen, halogen, hydroxy, etherified or esterified hydroxy, amino, mono- or disubstituted amino, cyano, nitro, mercapto, substituted mercapto, carboxy, esterified carboxy, carbamoyl, N-mono- or N,N-di-substituted carbamoyl, sulfo, substituted sulfonyl, aminosulfonyl or N-mono- or N,N-di-substituted aminosulfonyl;

n and m are, independently of one another, a number from and including 0 to and including 4;

$R_5$ is hydrogen, an aliphatic, carbocyclic, or carbocyclic-aliphatic radical with up to 29 carbon atoms in each case, or a heterocyclic or heterocyclic-aliphatic radical with up to 20 carbon atoms in each case, and in each case up to 9 heteroatoms, or acyl with up to 30 carbon atoms;

X stands for 2 hydrogen atoms; for 1 hydrogen atom and hydroxy; for O; or for hydrogen and lower alkoxy;

Q and Q' are independently a pharmaceutically acceptable organic bone or hydrogen, halogen, hydroxy, etherified or esterified hydroxy, amino, mono- or disubstituted amino, cyano, nitro, mercapto, substituted mercapto, carboxy, esterified carboxy, carbamoyl, N-mono- or N,N-di-substituted carbamoyl, sulfo, substituted sulfonyl, aminosulfonyl or N-mono- or N,N-di-substituted aminosulfonyl;

or a salt thereof, if at least one salt-forming group is present, or hydrogenated derivative thereof, for the preparation of a pharmaceutical composition for the treatment of diseases involving deregulated FLT3 receptor tyrosine kinase activity.

The term "organic bone" as used herein refers to a pharmacologically acceptable organic chemical structure, such as but not limited to hydrocarbyl radical or an acyl radical Ac, which radicals preferably have a maximum of 30 carbon atoms.

The hydrocarbyl radical (hydrocarbon radical) is an acyclic (aliphatic), carbocyclic or carbocyclic-acyclic hydrocarbon radical having a maximum total number of carbon atoms of preferably 30 and, especially, 18, which may be saturated or unsaturated, unsubstituted or substituted. It may also contain instead of one, two or more carbon atoms the same or different hetero atoms, such as, especially, oxygen, sulphur and nitrogen, in the acyclic and/or cyclic moiety; in the latter case it is referred to as a heterocyclic radical (heterocyclyl radical) or a heterocyclic-acyclic radical.

Unsaturated radicals are those that contain one or more, especially conjugated and/or isolated, multiple bonds (double and/or triple bonds). The term "cyclic radicals" also includes aromatic radicals, for example those in which at least one 6-membered carbocyclic ring or one 5- to 8-membered heterocyclic ring contains the maximum number of non-cumulated double bonds. Carbocyclic radicals in which at least one ring is in the form of a 6-membered aromatic ring (that is to say a benzene ring) are referred to as aryl radicals. An acyclic unsubsbtuted hydrocarbon radical is especially a straight or branched lower alkyl, lower alkenyl, lower alkadienyl or lower alkynyl radical. In corresponding unsaturated radicals, the double bond is located especially in a position higher than the .alpha.-position to the free valency.

A carbocyclic hydrocarbon radical is especially a mono-, bi- or polycyclic cycloalkyl, cycloalkenyl or cycloalkadienyl radical, or a corresponding aryl radical. Preferred are radicals having a maximum of 14, especially 12, ring carbon atoms and having 3- to 8-membered, preferably 5 to 7-membered, especially 6-membered, rings; they may also carry one or more, for example two, acyclic radicals, for example those mentioned above, and especially lower alkyl radicals, or other carbocyclic radicals. Carbocyclic-acyclic radicals are those in which an acyclic radical, especially one having a maximum of 10, preferably a maximum of 6, carbon atoms, such as, especially, methyl, ethyl or vinyl, carries one or more of the carbocyclic, optionally aromatic radicals defined above. Mention is made especially of cycloalkyl-lower alkyl and aryl-lower alkyl radicals, and also analogues thereof unsaturated in the ring and/or chain, that carry the ring at the terminal carbon atom of the chain.

Linkers between the acyclic (aliphatic) or carbocyclic radicals may be selected from, but not limited to, straight or branched lower alkyl, lower alkenyl, lower alkadienyl or lower alkynyl radical, etherified or esterified hydroxy, amino, —O—, —S—, carbonyl, carbonyidioxy, —NO—, —SO—, mono- or disubstituted amino, cyano, nitro, mercapto, substituted mercapto, carboxy, esterified carboxy, carbamoyl, N-mono- or N,N-di-substituted carbamoyl, sulfo, substituted sulfonyl, aminosulfonyl or N-mono- or N,N-di-substituted aminosulfonyl.

The invention relates in particular to the use of staurosporines derivatives of formula,

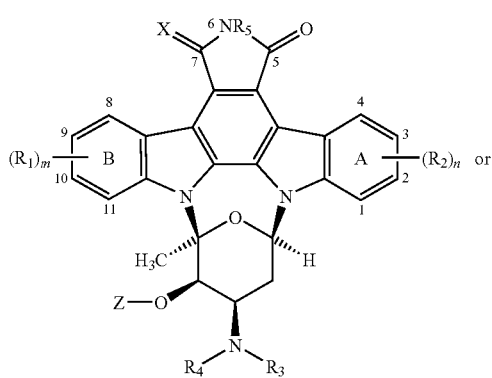
(I)

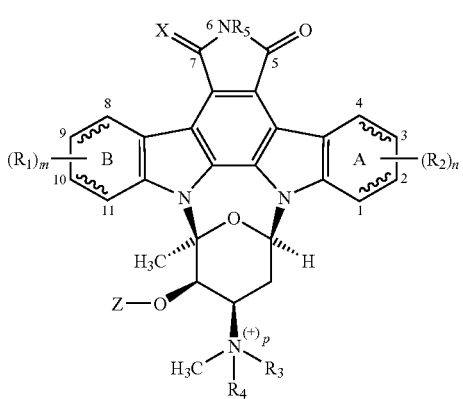
(II)

(II) which is the partially hydrogenated derivative of compound (I),

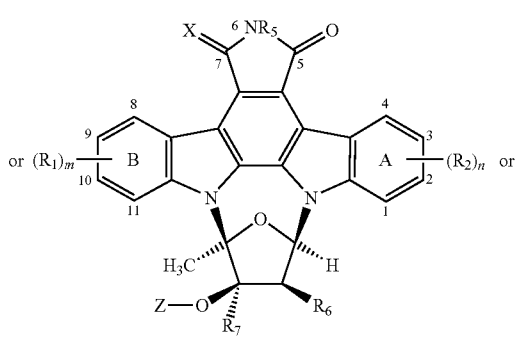
(III) or

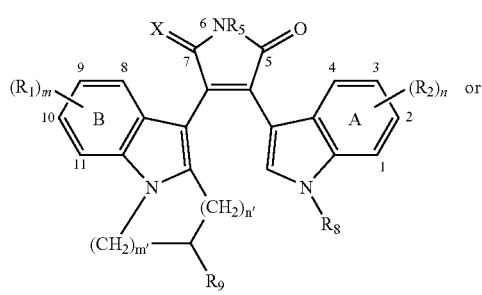
(IV) or

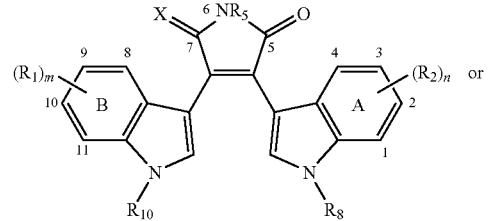
(V) or

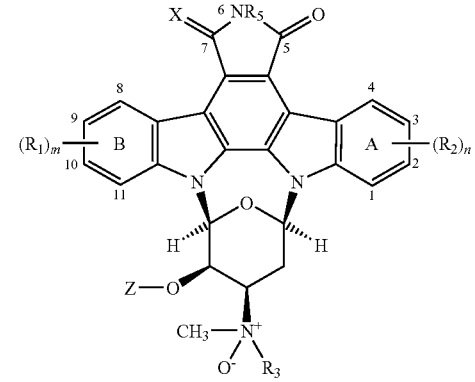
(VI)

wherein $R_1$ and $R_2$, are, independently of one another, unsubstituted or substituted alkyl, hydrogen, halogen, hydroxy, etherified or esterified hydroxy, amino, mono- or disubstituted amino, cyano, nitro, mercapto, substituted mercapto, carboxy, esterified carboxy, carbamoyl, N-mono- or N,N-di-substituted carbamoyl, sulfo, substituted sulfonyl, aminosulfonyl or N-mono- or N,N-di-substituted aminosulfonyl;

n and m are, independently of one another, a number from and including 0 to and including 4;

n' and m' are, independently of one another, a number from and including 0 to and including 4;

$R_3$, $R_4$, $R_8$ and $R_{10}$ are, independently of one another, hydrogen, —O$^-$, acyl with up to 30 carbon atoms, an aliphatic, carbocyclic, or carbocyclic-aliphatic radical with up to 29 carbon atoms in each case, a heterocyclic or heterocyclic-aliphatic radical with up to 20 carbon atoms in each case, and in each case up to 9 heteroatoms, an acyl with up to 30 carbon atoms, wherein $R_4$ may also be absent;

or if $R_3$ is acyl with up to 30 carbon atoms, $R_4$ is not an acyl;

p is 0 if $R_4$ is absent, or is 1 if $R_3$ and $R_4$ are both present and in each case are one of the aforementioned radicals;

$R_5$ is hydrogen, an aliphatic, carbocyclic, or carbocyclic-aliphatic radical with up to 29 carbon atoms in each case, or a heterocyclic or heterocyclic-aliphatic radical with up to 20 carbon atoms in each case, and in each case up to 9 heteroatoms, or acyl with up to 30 carbon atoms;

$R_7$, $R_6$ and $R_9$ are acyl or -(lower alkyl)-acyl, unsubstituted or substituted alkyl, hydrogen, halogen, hydroxy, etherified or esterified hydroxy, amino, mono- or disubstituted amino, cyano, nitro, mercapto, substituted mercapto, carboxy,carbonyl, carbonyldioxy, esterified carboxy, carbamoyl, N-mono- or N,N-di-substituted carbamoyl, sulfo, substituted sulfonyl, aminosulfonyl or N-mono- or N,N-disubstituted aminosulfonyl;

X stands for 2 hydrogen atoms; for 1 hydrogen atom and hydroxy; for O; or for hydrogen and lower alkoxy;

Z stands for hydrogen or lower alkyl;

and either the two bonds characterised by wavy lines are absent in ring A and replaced by 4 hydrogen atoms, and the two wavy lines in ring B each, together with the respective parallel bond, signify a double bond;

or the two bonds characterised by wavy lines are absent in ring B and replaced by a total of 4 hydrogen atoms, and the two wavy lines in ring A each, together with the respective parallel bond, signify a double bond;

or both in ring A and in ring B all of the 4 wavy bonds are absent and are replaced by a total of 8 hydrogen atoms;

or a salt thereof, if at least one salt-forming group is present for the preparation of a pharmaceutical composition for the treatment of diseases involving deregulated FLT3 receptor tyrosine kinase activity.

The general terms and definitions used preferably have hereinbefore and hereinafter the following meanings:

The prefix "lower" indicates that the associated radical preferably has up to and including a maximum of 7 carbon atoms, especially up to and including a maximum of 4 carbon atoms.

Lower alkyl is especially methyl, ethyl, n-propyl, isopropyl, n-butyl, isobutyl, sec-butyl, or tert-butyl, and also pentyl, hexyl, or heptyl.

Unsubstituted or substituted alkyl is preferably $C_1$-$C_{20}$alkyl, especially lower alkyl, typically methyl, ethyl, n-propyl, isopropyl, n-butyl, isobutyl, sec-butyl, or tert-butyl, which is unsubstituted or substituted especially by halogen, such as fluorine, chlorine, bromine, or iodine, $C_6$-$C_{14}$aryl, such as phenyl or naphthyl, hydroxy, etherified hydroxy, such as lower alkoxy, phenyl-lower alkoxy or phenyloxy, esterified hydroxy, such as lower alkanoyloxy or benzoyloxy, amino, mono- or disubstituted amino, such as lower alkylamino, lower alkanoylamino, phenyl-lower alkylamino, N,N-di-lower alkylamino, N,N-di-(phenyl-lower alkyl)amino, cyano, mercapto, substituted mercapto, such as lower alkylthio, carboxy, esterified carboxy, such as lower alkoxycarbonyl, carbamoyl, N-mono- or N,N-disubstituted carbamoyl, such as N-lower alkylcarbamoyl or N,N-di-lower alkylcarbamoyl, sulfo, substituted sulfo, such as lower alkanesulfonyl or lower alkoxysulfonyl, aminosulfonyl or N-mono- or N,N-disubstituted aminosulfonyl, such as N-lower alkylaminosulfonyl or N,N-di-lower alkylaminosulfonyl.

Halogen is preferably fluorine, chlorine, bromine, or iodine, especially fluorine or chlorine.

Etherified hydroxy is especially lower alkoxy, $C_6$-$C_{14}$aryloxy, such as phenyloxy, or $C_6$-$C_{14}$aryl-lower alkoxy, such as benzyloxy.

Esterified hydroxy is preferably lower alkanoyloxy or $C_6$-$C_{14}$arylcarbonyloxy, such as benzoyloxy.

Mono- or disubstituted amino is especially amino monosubstituted or disubstituted by lower alkyl, $C_6$-$C_{14}$aryl, $C_6$-$C_{14}$aryl-lower alkyl, lower alkanoyl, or $C_6$-$C_{12}$arylcarbonyl.

Substituted mercapto is especially lower alkylthio, $C_6$-$C_{14}$arylthio, $C_6$-$C_{14}$aryl-lower alkylthio, lower alkanoylthio, or $C_6$-$C_{14}$aryl-lower alkanoylthio.

Esterified carboxy is especially lower alkoxycarbonyl, $C_6$-$C_{14}$aryl-lower alkoxycarbonyl or $C_6$-$C_{14}$aryloxycarbonyl.

N-Mono- or N,N-disubstituted carbamoyl is especially carbamoyl N-monosubstituted or N,N-disubstituted by lower alkyl, $C_6$-$C_{14}$aryl or $C_6$-$C_{14}$aryl-lower alkyl.

Substituted sulfonyl is especially $C_6$-$C_{14}$arylsulfonyl, such as toluenesulfonyl, $C_6$-$C_{14}$aryl-lower alkanesulfonyl or lower alkanesulfonyl.

N-Mono- or N,N-disubstituted aminosulfonyl is especially aminosulfonyl N-monosubstituted or N,N-disubstituted by lower alkyl, $C_6$-$C_{14}$aryl or $C_6$-$C_{14}$aryl-lower alkyl.

$C_6$-$C_{14}$Aryl is an aryl radical with 6 to 14 carbon atoms in the ring system, such as phenyl, naphthyl, fluorenyl, or indenyl, which is unsubstituted or is substituted especially by halogen, such as fluorine, chlorine, bromine, or iodine, phenyl or naphthyl, hydroxy, lower alkoxy, phenyl-lower alkoxy, phenyloxy, lower alkanoyloxy, benzoyloxy, amino, lower alkylamino, lower alkanoylamino, phenyl-lower alkylamino, N,N-di-lower alkylamino, N,N-di-(phenyl-lower alkyl) amino, cyano, mercapto, lower alkylthio, carboxy, lower alkoxycarbonyl, carbamoyl, N-lower alkylcarbamoyl, N,N-di-lower alkylcarbamoyl, sulfo, lower alkanesulfonyl, lower alkoxysulfonyl, aminosulfonyl, N-lower alkylaminosulfonyl, or N,N-di-lower alkylaminosulfonyl.

The indices n and m are in each case preferably 1, 2 or especially 0. In general, compounds of formula I in which n and m are in each case 0 (zero) are especially preferred.

An aliphatic carbohydrate radical with up to 29 carbon atoms $R_3$, $R_4$, $R_8$ or $R_{10}$, which is substituted by acyclic substituents and preferably has a maximum of 18, especially a maximum of 12, and as a rule not more than 7 carbon atoms, may be saturated or unsaturated and is especially an unsubstituted or a straight-chain or branched lower alkyl, lower alkenyl, lower alkadienyl, or lower alkinyl radical substituted by acyclic substituents. Lower alkyl is, for example, methyl, ethyl, n-propyl, isopropyl, n-butyl, isobutyl, sec-butyl or tert-butyl, and also n-pentyl, isopentyl, n-hexyl, isohexyl and n-heptyl; lower alkenyl is, for example, allyl, propenyl, isopropenyl, 2- or 3-methallyl and 2- or 3-butenyl; lower alkadienyl is, for example, 1-penta-2,4-dienyl; lower alkinyl is, for example, propargyl or 2-butinyl. In corresponding unsaturated radicals, the double bond is especially located in a position higher than the α-position in relation to the free valency. Substituents are especially the acyl radicals defined hereinbelow as substituents of R°, preferably free or esterified carboxy, such as carboxy or lower alkoxycarbonyl, cyano or di-lower alkylamino.

A carbocyclic or carbocyclic-aliphatic radical $R_3$, $R_4$, $R_8$ or $R_{10}$ with up to 29 carbon atoms in each case is especially an aromatic, a cycloaliphatic, a cycloaliphatic-aliphatic, or an aromatic-aliphatic radical which is either present in unsubstituted form or substituted by radicals referred to hereinbelow as substituents of R°. An aromatic radical (aryl radical) $R_3$ or $R_4$ is most especially a phenyl, also a naphthyl, such as 1- or 2-naphthyl, a biphenylyl, such as especially 4-biphenylyl, and also an anthryl, fluorenyl and azulenyl, as well as their aromatic analogues with one or more saturated rings, which is either present in unsubstituted form or substituted by radicals referred to hereinbelow as substituents of R°. Preferred aromatic-aliphatic radicals are aryl-lower alkyl- and aryl-lower alkenyl radicals, e.g. phenyl-lower alkyl or phenyl-lower alkenyl with a terminal phenyl radical, such as for example benzyl, phenethyl, 1-, 2-, or 3-phenylpropyl, diphenylmethyl (benzhydryl), trityl, and cinnamyl, and also 1- or 2-naphthylmethyl. Of aryl radicals carrying acyclic radicals, such as lower alkyl, special mention is made of o-, m- and p-tolyl and xylyl radicals with variously situated methyl radicals.

A cycloaliphatic radical $R_3$, $R_4$, $R_8$ or $R_{10}$ with up to 29 carbon atoms is especially a substituted or preferably unsubstituted mono-, bi-, or polycyclic cycloalkyl-, cycloalkenyl-, or cycloalkadienyl radical. Preference is for radicals with a maximum of 14, especially 12, ring-carbon atoms and 3- to 8-, preferably 5- to 7-, and most especially 6-member rings which can also carry one or more, for example two, aliphatic hydrocarbon radicals, for example those named above, especially the lower alkyl radicals, or other cycloaliphatic radicals. Preferred substituents are the acyclic substituents named hereinbelow for $R^o$.

A cycloaliphatic-aliphatic radical $R_3$, $R_4$, $R_8$ or $R_{10}$ with up to 29 carbon atoms is a radical in which an acyclic radical, especially one with a maximum of 7, preferably a maximum of 4 carbon atoms, such as especially methyl, ethyl, and vinyl, carries one or more cycloaliphatic radicals as defined hereinabove. Special mention is made of cycloalkyl-lower alkyl radicals, as well as their analogues which are unsaturated in the ring and/or in the chain, but are non-aromatic, and which carry the ring at the terminal carbon atom of the chain. Preferred substituents are the acyclic substituents named herein below for $R^o$.

Heterocyclic radicals $R_3$, $R_4$, $R_8$ or $R_{10}$ with up to 20 carbon atoms each and up to 9 heteroatoms each are especially monocyclic, but also bi- or polycyclic, aza-, thia-, oxa-, thiaza-, oxaza-, diaza-, triaza-, or tetrazacyclic radicals of an aromatic character, as well as corresponding heterocyclic radicals of this type which are partly or most especially wholly saturated, these radicals—if need be—possibly carrying further acyclic, carbocyclic, or heterocyclic radicals and/or possibly mono-, di-, or polysubstituted by functional groups, preferably those named hereinabove as substituents of aliphatic hydrocarbon radicals. Most especially they are unsubstituted or substituted monocyclic radicals with a nitrogen, oxygen, or sulfur atom, such as 2-aziridinyl, and especially aromatic radicals of this type, such as pyrryl, for example 2-pyrryl or 3-pyrryl, pyridyl, for example 2-, 3-, or 4-pyridyl, and also thienyl, for example 2- or 3-thienyl, or furyl, for example 2-furyl; analogous bicyclic radicals with an oxygen, sulfur, or nitrogen atom are, for example, indolyl, typically 2- or 3-indolyl, quinolyl, typically 2- or 4-quinolyl, isoquinolyl, typically 3- or 5-isoquinolyl, benzofuranyl, typically 2-benzofuranyl, chromenyl, typically 3-chromenyl, or benzothienyl, typically 2- or 3-benzothienyl; preferred monocyclic and bicyclic radicals with several heteroatoms are, for example, imidazolyl, typically 2- or 4-imidazolyl, pyrimidinyl, typically 2-or 4-pyrimidinyl, oxazolyl, typically 2-oxazolyl, isoxazolyl, typically 3-isoxazolyl, or thiazolyl, typically 2-thiazolyl, and benzimidazolyl, typically 2-benzimidazolyl, benzoxazolyl, typically 2-benzoxazolyl, or quinazolyl, typically 2-quinazolinyl. Appropriate partially or, especially, completely saturated analogous radicals may also be considered, such as 2-tetrahydrofuryl, 2- or 3-pyrrolidinyl, 2-, 3-, or 4-piperidyl, and also 2-or 3-morpholinyl, 2- or 3-thiomo 2-piperazinyl and N-mono- or N,N'-bis-lower alkyl-2-piperazinyl radicals. These radicals may also carry one or more acyclic, carbocyclic, or heterocyclic radicals, especially those mentioned hereinabove. The free valency of the heterocyclic radicals $R_3$ or $R_4$ must emanate from one of their carbon atoms. Heterocyclyl may be unsubsttuted or substituted by one or more, preferably one or two, of the substituents named hereinbelow for $R^o$.

Heterocyclic-aliphatic radicals $R_3$, $R_4$, $R_8$ or $R_{10}$ especially lower alkyl radicals, especially with a maximum of 7, preferably a maximum of 4 carbon atoms, for example those named hereinabove, which carry one, two, or more heterocyclic radicals, for example those named in the preceding paragraph, the heterocyclic ring possibly being linked to the aliphatic chain also by one of its nitrogen atoms. A preferred heterocyclic-aliphatic radical $R_1$ is, for example, imidazol-1-ylmethyl, 4-methylpiperazin-1-ylmethyl, piperazin-1-ylmethyl, 2-(morpholin4-yl)ethyl and also pyrid-3-ylmethyl. Heterocyclyl may be unsubstituted or substituted by one or more, preferably one or two, of the substituents named hereinbelow for $R_o$.

A heteroaliphatic radical $R_3$, $R_4$, R or $R_{10}$ with up to 20 carbon atoms each and up to 10 heteroatoms each is an aliphatic radical which, instead of one, two, or more carbon atoms, contains identical or different heteroatoms, such as especially oxygen, sulfur, and nitrogen. An especially preferred arrangement of a heteroaliphabc radical $R_1$ takes the form of oxaalkyl radicals in which one or more carbon atoms are replaced in a preferably linear alkyl by oxygen atoms preferably separated from one another by several (especially 2) carbon atoms so that they form a repeating group, if need be multi-repeating group $(O-CH_2-CH_2-)_q$, wherein q=1 to 7.

Especially preferred as $R_3$, $R_4$, $R_8$ or $R_{10}$, apart from acyl, is lower alkyl, particlularly methyl or ethyl; lower alkoxycarbonyl-lower alkyl, especially methoxycarbonylmethyl or 2-(tert-butoxycarbonyl)ethyl; carboxy-lower alkyl, especially carboxymethyl or 2-carboxyethyl; or cyano-lower alkyl, especially 2-cyanoethyl.

An acyl radical $R_3$, $R_4$, $R_6$, $R_7$, $R_8$, $R_9$, or $R_{10}$ with up to 30 carbon atoms derives from a carboxylic acid, functionally modified if need be, an organic sulfonic acid, or a phosphoric acid, such as pyro- or orthophosphoric acid, esterified if need be.

An acyl designated $Ac^1$ and derived from a carboxylic acid, functionally modified if need be, is especially one of the subformula $Y-C(=W)-$, wherein W is oxygen, sulfur, or imino and Y is hydrogen, hydrocarbyl $R^o$ with up to 29 carbon atoms, hydrocarbyloxy $R^o-O-$, an amino group or a substituted amino group, especially one of the formula $R^oHN-$ or $R^oR^oN-$ (wherein the $R^o$ radicals may be identical or different from one another).

The hydrocarbyl (hydrocarbon radical) $R^o$ is an acyclic (aliphatic), carbocyclic, or carbocyclic-acyclic hydrocarbon radical, with up to 29 carbon atoms each, especially up to 18, and preferably up to 12 carbon atoms, and is saturated or unsaturated, unsubstituted or substituted. Instead of one, two, or more carbon atoms, it may contain identical or different heteroatoms, such as especially oxygen, sulfur, and nitrogen in the acyclic and/or cyclic part; in the latter case, it is described as a heterocyclic radical (heterocyclyl radical) or a hetero-cyclic-acyclic radical.

Unsaturated radicals are those, which contain one or more, especially conjugated and/or isolated, multiple bonds (double or triple bonds). The term cyclic radicals includes also aromatic and non-aromatic radicals with conjugated double bonds, for example those wherein at least one 6-member carbocyclic or a 5- to 8-member heterocyclic ring contains the maximum number of non-cumulative double bonds. Carbocyclic radicals, wherein at least one ring is present as a 6-member aromatic ring (i.e. a benzene ring), are defined as aryl radicals.

An acyclic unsubstituted hydrocarbon radical $R^o$ is especially a straight-chained or branched lower alkyl-, lower alkenyl-, lower alkadienyl-, or lower alkinyl radical. Lower alkyl $R^o$ is, for example, methyl, ethyl, n-propyl, isopropyl, n-butyl, isobutyl, sec-butyl or tert-butyl, and also n-pentyl, isopentyl, n-hexyl, isohexyl and n-heptyl; lower alkenyl is, for example, allyl, propenyl, isopropenyl, 2- or 3-methallyl and 2- or 3-butenyl; lower alkadienyl is, for example, 1-penta-2,4dienyl; lower alkinyl is, for example, propargyl or 2-butinyl. In corresponding unsaturated radicals, the double bond is especially located in a position higher than the α-position in relation to the free valency.

A carbocyclic hydrocarbon radical R° is especially a mono-, bi-, or polycyclic cycloalkyl-, cycloalkenyl-, or cycloalkadienyl radical, or a corresponding aryl radical. Preference is for radicals with a maximum of 14, especially 12, ring-carbon atoms and 3- to B, preferably 5 to 7-, and most especially 6-member rings which can also carry one or more, for example two, acyclic radicals, for example those named above, especially the lower alkyl radicals, or other carbocyclic radicals. Carbocyclic-acyclic radicals are those in which an acyclic radical, especially one with a maximum of 7, preferably a maximum of 4 carbon atoms, such as especially methyl, ethyl and vinyl, carries one or more carbocydic, if need be aromatic radicals of the above definition. Special mention is made of cycloalkyl-lower and aryl-lower alkyl radicals, as well as their analogues which are unsaturated in the ring and/or chain, and which carry the ring at the terminal carbon atom of the chain.

Cycloalkyl R° has most especially from 3 up to and including 10 carbon atoms and is, for example, cyclopropyl, cyclobutyl, cyclopentyl, cyciohexyl, cycloheptyl, and cyclooctyl, as well as bicyclo[2,2,2]octyl, 2-bicyclo[2,2,1]heptyl, and adamantyl, which may also be substituted by 1, 2, or more, for example lower, alkyl radicals, especially methyl radicals; cycloalkenyl is for example one of the monocyclic cycloalkyl radicals already named which carries a double bond in the 1-, 2-, or 3 position. Cycloalkyl-lower alkyl or -lower alkenyl is for example a -methyl, -1- or -2-ethyl, -1- or -2-vinyl, -1-, -2-, or -3-propyl or -allyl substituted by one of the above-named cycloalkyl radicals, those substituted at the end of the linear chain being preferred.

An aryl radical R° is most especially a phenyl, also a naphthyl, such as 1- or 2-naphthyl, a biphenylyl, such as especially 4-biphenylyl, and also an anthryl, fluorenyl and azulenyl, as well as their aromatic analogues with one or more saturated rings. Preferred aryl-lower alkyl and -lower alkenyl radicals are, for example, phenyl-lower alkyl or phenyl-lower alkenyl with a terminal phenyl radical, such as for example benzyl, phenethyl, 1-, 2-, or 3phenylpropyl, diphenylmethyl (benzhydryl), trityl, and cinnamyl, and also 1- or 2-naphthylmethyl. Aryl may be unsubstituted or substituted.

Heterocyclic radicals, including heterocyclic-acyclic radicals, are especially monocyclic, but also bi- or polycyclic, aza-, thia-, oxa-, thiaza-, oxaza-, diaza-, triaza-, or tetrazacyclic radicals of an aromatic character, as well as corresponding heterocyclic radicals of this type which are partly or most especially wholly saturated; if need be, for example as in the case of the above-mentioned carbocyclic or aryl radicals, these radicals may carry further acyclic, carbocyclic, or heterocyclic radicals and/or may be mono-, di-, or polysubstituted by functional groups. The acyclic part in heterocyclic-acyclic radicals has for example the meaning indicated for the corresponding carbocyclic-acyclic radicals. Most especially they are unsubstituted or substituted monocyclic radicals with a nitrogen, oxygen, or sulfur atom, such as 2-aziridinyl, and especially aromatic radicals of this type, such as pyrrolyl, for example 2-pyrrolyl or 3-pyrrolyl, pyridyl, for example 2-, 3-, or 4-pyridyl, and also thienyl, for example 2- or 3-thienyl, or furyl, for example 2-furyl; analogous bicyclic radicals with an oxygen, sulfur, or nitrogen atom are, for example, indolyl, typically 2- or 3-indolyl, quinolyl, typically 2- or 4-quinolyl, isoquinolyl, typically 3- or 5-isoquinolyl, benzofuranyl, typically 2-benzofuranyl, chromenyl, typically 3-chromenyl, or benzothienyl, typically 2- or 3-benzothienyl; preferred monocyclic and bicyclic radicals with several heteroatoms are, for example, imidazolyl, typically 2-imidazolyl, pyrimidinyl, typically 2-or 4-pyrimidinyl, oxazolyl, typically 2-oxazolyl, isoxazolyl, typically 3-isoxazolyl, or thiazolyl, typically 2-thiazolyl, and benzimidazolyl, typically 2-benzimidazolyl, benzoxazolyl, typically 2-benzoxazolyl, or quinazolyl, typically 2-quinazolinyl. Appropriate partially or, especially, completely saturated analogous radicals may also be considered, such as 2-tetrahydrofuryl, 4-tetrahydrofuryl, 2-or 3-pyrrolidyl, 2-, 3-, or 4-piperidyl, and also 2-or 3-morpholinyl, 2- or 3-thiomorpholinyl, piperazinyl, and N,N'-bis-lower alkyl-2-piperazinyl radicals. These radicals may also carry one or more acyclic, carbocyclic, or heterocyclic radicals, especially those mentioned hereinabove. Heterocyclic-acyclic radicals are especially derived from acyclic radicals with a maximum of 7, preferably a maximum of 4 carbon atoms, for example those named hereinabove, and may carry one, two, or more heterocyclic radicals, for example those named hereinabove, the ring possibly being linked to the aliphatic chain also by one of its nitrogen atoms.

As already mentioned, a hydrocarbyl (including a heterocyclyl) may be substituted by one, two, or more identical or different substituents (functional groups); one or more of the following substituents may be considered: lower alkyl; free, etherified and esterified hydroxyl groups; carboxy groups and esterified carboxy groups; mercapto- and lower alkylthio- and, if need be, substituted phenylthio groups; halogen atoms, typically chlorine and fluorine, but also bromine and iodine; halogen-lower alkyl groups; oxo groups which are present in the form of formyl (i.e. aldehydo) and keto groups, also as corresponding acetals or ketals; azido groups; nitro groups; cyano groups; primary, secondary and preferably tertiary amino groups, amino-lower alkyl, mono- or disubstituted amino-lower alkyl, primary or secondary amino groups protected by conventional protecting groups (especially lower alkoxycarbonyl, typically tert-butoxycarbonyl) lower alkylenedioxy, and also free or functionally modified sulfo groups, typically sulfamoyl or sulfo groups present in free form or as salts. The hydrocarbyl radical may also carry carbamoyl, ureido, or guanidino groups, which are free or which carry one or two substituents, and cyano groups. The above use of the word "groups" is taken to imply also an individual group.

Halogen-lower alkyl contains preferably 1 to 3 halogen atoms; preferred is trifluoromethyl or chloromethyl.

An etherified hydroxyl group present in the hydrocarbyl as substituent is, for example, a lower alkoxy group, typically the methoxy-, ethoxy-, propoxy-, isopropoxy-, butoxy-, and tert-butoxy group, which may also be substituted, especially by (i) heterocyclyl, whereby heterocyclyl can have preferably 4 to 12 ring atoms, may be unsaturated, or partially or wholly saturated, is mono- or bicyclic, and may contain up to three heteroatoms selected from nitrogen, oxygen, and sulfur, and is most especially pyrrolyl, for example 2-pyrrolyl or 3-pyrrolyl, pyridyl, for example 2-, 3- or 4-pyridyl, and also thienyl, for example 2- or 3-thienyl, or furyl, for example 2-furyl, indolyl, typically 2- or 3-indolyl, quinolyl, typically 2- or 4-quinolyl, isoquinolyl, typically 3- or 5-isoquinolyl, benzofuranyl, typically 2-benzofuranyl, chromenyl, typically 3-chromenyl, benzothienyl, typically 2- or 3-benzothienyl; imidazolyl, typically 1- or 2-imidazolyl, pyrimidinyl, typically 2-or 4-pyrimidinyl, oxazolyl, typically 2-oxazolyl, isoxazolyl, typically 3-isoxazolyl, thiazolyl, typically 2-thiazolyl, benzimidazolyl, typically 2-benzimidazolyl, benzoxazolyl, typically 2-benzoxazolyl, quinazolyl, typically 2quinazolinyl, 2-tetrahydrofuryl, 4-tetrahydrofuryl, 2- or 4-tetrahydropyranyl, 1-, 2- or 3-pyrrolidyl, 1-, 2-, 3-, or 4-piperidyl, 1-, 2-or 3-morpholinyl, 2- or 3-thiomorpholinyl, 2-piperazinyl or N,N'-bis-lower alkyl-2-piperazinyl; and also (ii) by halogen atoms, for example mono-, di-, or polysubstituted especially in the 2-position, as in the 2,2,2-trichloroethoxy, 2-chloroethoxy, or 2-Iodoethoxy radical, or (iii) by hydroxy or (iv) lower alkoxy radicals, each preferably monosubstituted, especially in the 2-position, as in the 2-methoxyethoxy radical. Such etherified hydroxyl groups are also unsubstituted or substituted phenoxy radicals and phenyl-lower alkoxy radicals, such as especially benzyloxy, benzhydryloxy, and triphenylmethoxy (trityloxy), as well as heterocyclyloxy radicals, wherein heterocyclyl can have preferably 4 to 12 ring atoms, may be unsaturated, or partially or wholly saturated, is mono- or bicyclic, and may contain up to three heteroatoms selected from nitrogen, oxygen, and sulfur, and is most especially pyrrolyl, for example 2-pyrrolyl or 3-pyrrolyl, pyridyl, for example 2-, 3- or 4pyridyl, and also thienyl, for example 2- or 3-thienyl, or furyl, for example 2-furyl, indolyl, typically 2- or 3-indolyl, quinolyl, typically 2- or 4-quinolyl, isoquinolyl, typically 3- or 5-isoquinolyl, benzofuranyl, typically 2-benzofuranyl, chromenyl, typically 3-chromenyl, benzothienyl, typically 2- or 3-benzothienyl; imidazolyl, typically 1- or 2-imidazolyl, pyrimidinyl, typically 2- or 4-pyrimidinyl, oxazolyl, typically 2-oxazolyl, isoxazolyl, typically 3-isoxazolyl, thiazolyl, typically 2-thiazolyl, benzimidazolyl, typically 2-benzimidazolyl, benzoxazolyl, typically 2-benzoxazolyl, quinazolyl, typically 2-quinazolinyl, 2-tetrahydrofuryl, 4-tetrahydrofuryl, 2- or 4-tetrahydropyranyl, 1-, 2- or 3-pyrrolidyl, 1-, 2-, 3-, or 4-piperidyl, 1-, 2- or 3-morpholinyl, 2- or 3-thiomorpholinyl, 2-piperazinyl or N,N'-bis-lower alkyl-2-piperazinyl; such as especially 2- or 4-tetrahydropyranyloxy.

Etherified hydroxyl groups in this context are taken to include silylated hydroxyl groups, typically for example tri-lower alkylsilyloxy, typically trimethylsilyloxy and dimethyl-tert-butylsilyloxy, or phenyldi-lower alkylsilyloxy and lower alkyl-diphenylsilyloxy.

An esterified hydroxyl group present in the hydrocarbyl as a substituent is, for example, lower alkanoyloxy.

A carboxyl group present in the hydrocarbyl as a substituent is one in which the hydrogen atom is replaced by one of the hydrogen radicals characterised hereinabove, preferably a lower alkyl- or phenyl-lower alkyl radical; an example of an esterified carboxyl group is lower alkoxycarbonyl or phenyl-lower alkoxycarbonyl substituted if need be in the phenyl part, especially the methoxy, ethoxy, tert-butoxy, and benzyloxycarbonyl group, as well as a lactonised carboxyl group.

A primary amino group —NH$_2$ as substituent of the hydrocarbyls may also be present in a form protected by a conventional protecting group. A secondary amino group carries, instead of one of the two hydrogen atoms, a hydrocarbyl radical, preferably an unsubstituted one, typically one of the above-named, especially lower alkyl, and may also be present in protected form.

A tertiary amino group present in the hydrocarbyl as substituent carries 2 different or, preferably, identical hydrocarbyl radicals (including the heterocyclic radicals), such as the unsubstituted hydrocarbyl radicals characterised hereinabove, especially lower alkyl.

A preferred amino group is one with the formula $R_{11}, (R_{12})$N—, wherein $R_{11}$ and $R_{12}$ are independently in each case hydrogen, unsubstituted acyclic $C_1$-$C_7$-hydrocarbyl (such as especially $C_1$-$C_4$alkyl or $C_2$-$C_4$alkenyl) or monocyclic aryl, aralkyl, or aralkenyl, substituted if necessary by $C_1$-$C_4$-alkyl, $C_1$-$C_4$-alkoxy, halogen, and/or nitro, and having a maximum of 10 carbon atoms, where the carbon-containing radicals may be interlinked through a carbon-carbon bond or an oxygen atom, a sulfur atom, or a nitrogen atom substituted if necessary by hydrocarbyl. In such a case, they form a nitrogen-containing heterocyclic ring with the nitrogen atom of the amino group. The following are examples of especially preferred disubstituted amino groups: di-lower alkylamino, typically dimethylamino or diethylamino, pyrrolidino, imidazol-1-yl, piperidino, piperazino, 4-lower alkylpiperazino, morpholino, thiomorpholino and piperazino or 4-methylpiperazino, as well as diphenylamino and dibenzylamino substituted if need be, especially in the phenyl part, for example by lower-alkyl, lower-alkoxy, halogen, and/or nitro; of the protected groups, especially lower alkoxycarbonylamino, typically tert-butoxycarbonylamino, phenyl-lower alkoxycarbonylamino, typically 4methoxybenzyloxycarbonylamino, and 9-fluorenylmethoxycarbonylamino.

Amino-lower alkyl is most especially substituted in the 1-position of the lower alkyl chain by amino and is especially aminomethyl.

Mono- or disubstituted amino-lower alkyl is amino-lower alkyl substituted by one or two radicals, wherein amino-lower alkyl is most especially substituted by amino in the 1-position of the lower alkyl chain and is especially aminomethyl; the amino substituents here are preferably (if 2 substituents are present in the respective amino group independently of one another) from the group comprising lower alkyl, such as especially methyl, ethyl or n-propyl, hydroxy-lower alkyl, typically 2-hydroxyethyl, $C_3$-$C_8$cycloalkyl, especially cyciohexyl, amino-lower alkyl, typically 3-aminopropyl or 4-aminobutyl, N-mono- or N,N-di(lower alkyl)amino-lower alkyl, typically 3-(N,N-dimethylamino)propyl, amino, N-mono- or N,N-di-lower alkylamino and N-mono- or N,N-di-(hydroxy-lower alkyl)amino.

Disubstituted amino-lower alkyl is also a 5 or 6-membered, saturated or unsaturated heterocycyl bonded to lower alkyl via a nitrogen atom (preferably in the 1-position) and having 0 to 2, especially 0 or 1, other heteroatoms selected from oxygen, nitrogen, and sulfur, which is unsubstituted or substituted, especially by one or two radicals from the group comprising lower alkyl, typically methyl, and also oxo. Preferred here is pyrrolidino (1-pyrrolidinyl), piperidino (1-piperidinyl), piperazino (1-piperazinyl), 4-lower alkylpiperazino, typically 4-methylpiperazino, imidazolino (1-imidazolyl), morpholino (4-morpholinyl), or also thiomorpholino, S-oxo-thiomorpholino, or S,S-dioxothiomorpholino.

Lower alkylenedioxy is especially methylenedioxy.

A carbamoyl group carrying one or two substituents is especially aminocarbonyl (carbamoyl) which is substitiuted by one or two radicals at the nitrogen; the amino substituents here are preferably (if 2 substituents are present in the respective amino group independently of one another) from the group comprising lower alkyl, such as especially methyl, ethyl or n-propyl, hydroxy-lower alkyl, typically 2-hydroxyethyl, $C_3$-$C_8$cycloalkyl, especially cyclohexyl, amino-lower alkyl, typically 3-aminopropyl or 4-aminobutyl, N-mono- or N,N-di(lower alkyl)-amino-lower alkyl, typically 3-(N,N-dimethylamino)propyl, amino, N-mono- or N,N-di-lower alkylamino and N-mono- or N,N-di-(hydroxy-lower alkyl) amino; disubstituted amino in aminocarbamoyl is also a 5 or 6-membered, saturated or unsaturated heterocyclyl with a bonding nitrogen atom and 0 to 2, especially 0 or 1, other heteroatoms selected from oxygen, nitrogen, and sulfur, which is unsubstituted or substituted, especially by one or two radicals from the group comprising lower alkyl, typically methyl, and also oxo. Preferred here is pyrrolidino (1-pyrrolidinyl), piperidino (1-piperidinyl), piperazino (1-piperazinyl), 4-lower al-kylpiperazino, typically 4-methylpiperazino, imidazolino (1-imidazolyl), morpholino (4-morpho-linyl), or also thiomorpholino, S-oxo-thiomorpholino, or S,S-dioxothiomorpholino.

An acyl derived from an organic sulfonic acid, which is designated $Ac^2$, is especially one with the subformula $R^o$—$SO_2$—, wherein $R^o$ is a hydrocarbyl as defined above in the general and specific meanings, the latter also being generally preferred here. Especially preferred is lower alkylphenylsulfonyl, especially 4-toluenesulfonyl.

An acyl derived from a phosphoric acid, esterified if necessary, which is designated $Ac^3$, is especially one with the subformula $R^oO(R^oO)P(=O)$—, wherein the radicals $R^o$ are, independently of one another, as defined in the general and specific meanings indicated above.

Reduced data on substituents given hereinbefore and hereinafter are considered to be preferences.

Preferred compounds according to the invention are, for example, those wherein $R^o$ has the following preferred meanings: lower alkyl, especially methyl or ethyl, amino-lower alkyl, wherein the amino group is unprotected or is protected by a conventional amino protecting group—especially by lower alkoxycarbonyl, typically tert-lower alkoxycarbonyl, for example tert-butoxycarbonyl—e.g. aminomethyl, R,S-, R- or preferably S-1-aminoethyl, tert-butoxycarbonylaminomethyl or R,S-, R-, or preferably S-1-(tert-butoxycarbonylamino)ethyl, carboxy-lower alkyl, typically 2-carboxyethyl, lower alkoxycarbonyl-lower alkyl, typically 2-(tert-butoxycarbonyl)ethyl, cyano-lower alkyl, typically 2-cyanoethyl, tetrahydropyranyloxy-lower alkyl, typically 4-(tetrahydropyranyl)-oxymethyl, morpholino-lower alkyl, typically 2-(morpholino)ethyl, phenyl, lower alkylphenyl, typically 4-methylphenyl, lower alkoxyphenyl, typically 4-methoxyphenyl, imidazolyl-lower alkoxyphenyl, typically 4-[2-(imidazol-1-yl)ethyl)oyxphenyl, carboxyphenyl, typically 4-carboxyphenyl, lower alkoxycarbonylphenyl, typically 4-ethoxycarbonylphenyl or 4-methoxyphenyl, halogen-lower alkylphenyl, typically 4-chloromethylphenyl, pyrrolidinophenyl, typically 4-pyrrolidinophenyl, imidazol-1-ylphenyl, typically 4-(imidazolyl-1-yl)phenyl, piperazinophenyl, typically 4-piperazinophenyl, (4-lower alkylpiperazino)phenyl, typically 4-(4-methylpiperazino)phenyl, morpholinophenyl, typically 4-morpholinophenyl, pyrrolidino-lower alkylphenyl, typically 4-pyrrolidinomethylphenyl, imidazol-1-yl-lower alkylphenyl, typically 4-(imidazolyl-1-ylmethyl)phenyl, piperazino-lower alkylphenyl, typically 4-piperazinomethylphenyl, (4-lower alkylpiperazinomethyl)-phenyl, typically 4-(4-methylpiperazinomethyl)phenyl, morpholino-lower alkylphenyl, typically 4-morpholinomethylphenyl, piperazinocarbonylphenyl, typically 4-piperazinocarbonylphenyl, or (4-lower alkyl-piperazino) phenyl, typically 4-(4-methylpiperazino)phenyl. Preferred acyl radicals $Ac^1$ are acyl radicals of a carboxylic acid which are characterised by the subformula $R^o$—CO—, wherein $R^o$ has one of the above general and preferred meanings of the hydrocarbyl radical $R^o$. Especially preferred radicals $R^o$ here are lower alkyl, especially methyl or ethyl, amino-lower alkyl, wherein the amino group is unprotected or protected by a conventional amino protecting group, especially by lower alkoxycarbonyl, typically tert-lower alkoxycarbonyl, for example tert-butoxycarbonyl, e.g. aminomethyl, R,S-, R-, or preferably S-1-aminoethyl, tert-butoxycarbonylaminomethyl or R,S-, R-, or preferably S-1-(tert-butoxycarbonylamino)ethyl, carboxy-lower alkyl, typically 2-carboxyethyl, lower alkoxycarbonyl-lower alkyl, typically 2-(tert-butoxycarbonyl)ethyl, tetrahydropyranyloxy-lower alkyl, typically 4-(tetrahydropyranyl)oxymethyl, phenyl, imidazolyl-lower alkoxyphenyl, typically 4-[2-(imidazol-1-yl)ethyl]oyxphenyl, carboxyphenyl, typically 4-carboxyphenyl, lower alkoxycarbonylphenyl, typically 4-ethoxycarbonylphenyl, halogen-lower alkylphenyl, typically 4-chloromethylphenyl, imidazol-1-ylphenyl, typically 4-(imidazolyl-1-yl)phenyl, pyrrolidino-lower alkylphenyl, typically 4-pyrrolidinomethylphenyl, piperazino-lower alkylphenyl, typically 4-piperazinomethylphenyl, (4-lower alkylpiperazinomethyl)phenyl, typically 4-(4-methyl-piperazinomethyl)phenyl, morpholino-lower alkylphenyl, typically 4-morpholinomethylphenyl, piperazinocarbonylphenyl, typically 4-piperazinocarbonylphenyl, or (4-lower alkylpiperazino)-phenyl, typically 4-(4-methylpiperazino)phenyl.

A further preferred Acyl $Ac^1$ is derived from monoesters of carbonic acid and is characterised by the subformula $R^o$—O—CO—. The lower alkyl radicals, especially tert-butyl, are especially preferred hydrocarbyl radicals $R^o$ in these derivatives.

Another preferred Acyl $Ac^1$ is derived from amides of carbonic add (or also thiocarbonic acid) and is characterised by the formula $R^oHN$—$C(=W)$— or $R^oR^oN$—$C(=W)$—, wherein the radicals $R^o$ are, independently of one another, as defined above and W is sulfur and especially oxygen. In particular, compounds are preferred wherein $Ac^1$ is a radical of formula $R^oHN$—$C(=W)$—, wherein W is oxygen and $R^o$ has one of the following preferred meanings: morpholino-lower alkyl, typically 2-morpholinoethyl, phenyl, lower alkoxyphenyl, typically 4-methoxyphenyl or 4-ethoxyphenyl, carboxyphenyl, typically 4-carboxyphenyl, or lower alkoxycarbonylphenyl, typically 4-ethoxycarbonylphenyl.

A preferred acyl $Ac^2$ of subformula $R^o$—$SO_2$—, wherein $R^o$ is a hydrocarbyl as defined in the above general and specific meanings, is lower alkylphenylsulfonyl, typically 4-toluenesulfonyl.

If p is 0, the nitrogen atom bonding $R_3$ is uncharged. If p is 1, then $R_4$ must also be present, and the nitrogen atom bonding $R_3$ and $R_4$ (quaternary nitrogen) is then positively charged. The definitions for an aliphatic, carbocyclic, or carbocyclic-aliphatic radical with up to 29 carbon atoms each, or for a heterocyclic or heterocyclic-aliphatic radical with up to 20 carbon atoms each and up to 9 heteroatoms each, or acyl with up to 30 carbon atoms each, preferably match the definitions given for the corresponding radicals $R_3$ and $R_4$. Especially preferred is $R_5$ lower alkyl, especially methyl, or most especially hydrogen.

Z is especially lower alkyl, most especially methyl or hydrogen.

If the two bonds indicated by wavy lines are missing in ring A, then no double bonds (tetra-hydrogenated derivatives) are present between the carbon atoms characterised in formula I by the numbers 1, 2, 3, and 4, but only single bonds, whereas ring B is aromatic (double bonds between the carbon atoms characterised in formula I by 8 and 9 and those characterised by 10 and 11). If the two bonds indicated by wavy lines are missing in ring B, then no double bonds (tetra-hydrogenated derivatives) are present between the carbon atoms characterised in formula I by the numbers 8, 9, 10, and 11, but only single bonds, whereas ring A is aromatic (double bonds between the carbon atoms characterised in formula I by 1 and 2 and those characterised by 3 and 4). If the total of four bonds indicated by wavy lines are missing in rings A and B, and are replaced by a total of 8 hydrogen atoms, then no double bonds (octa-hydrogenated derivatives) are present between the carbon atoms numbered 1, 2, 3, 4, 8, 9, 10, and 11 in formula I, but only single bonds.

By their nature, the compounds of the invention may also be present in the form of pharmaceutically, i.e. physiologically, acceptable salts, provided they contain salt-forming groups. For isolation and purification, pharmaceutically unacceptable salts may also be used. For therapeutic use, only pharmaceutically acceptable salts are used, and these salts are preferred.

Thus, compounds of formula I having free acid groups, for example a free sulfo, phosphoryl or carboxyl group, may exist as a salt, preferably as a physiologically acceptable salt with a salt-forming basic component. These may be primarily metal or ammonium salts, such as alkali metal or alkaline earth metal salts, for example sodium, potassium, magnesium or calcium salts, or ammonium salts with ammonia or suitable organic amines, especially tertiary monoamines and heterocyclic bases, for example triethylamine, tri-(2-hydroxyethyl)-amine, N-ethylpiperidine or N,N'-dimethylpiperazine.

Compounds of the invention having a basic character may also exist as addition salts, especially as acid addition salts with inorganic and organic acids, but also as quaternary salts. Thus, for example, compounds which have a basic group, such as an amino group, as a substituent may form acid addition salts with common acids. Suitable acids are, for example, hydrohalic acids, e.g. hydrochloric and hydrobromic acid, sulfuric acid, phosphoric acid, nitric acid or perchloric acid, or aliphatic, alicyclic, aromatic or heterocyclic carboxylic or sulfonic acids, such as formic, acetic, propionic, succinic, glycolic, lactic, malic, tartaric, citric, fumaric, maleic, hydroxymaleic, oxalic, pyruvic, phenylacetic, benzoic, p-aminobenzoic, anthranilic, p-hydroxybenzoic, salicylic, p-aminosalicylic acid, pamoic acid, methanesulfonic, ethanesulfonic, hydroxyethanesulfonic, ethylenedisulfonic, halobenzenesulfonic, toluenesulfonic, naphthalenesulfonic acids or sulfanilic acid, and also methionine, tryptophan, lysine or arginine, as well as ascorbic acid.

In view of the close relationship between the novel compounds (especially of formula I) in free form and in the form of their salts, including those salts that can be used as intermediates, for example in the purification or identification of the novel compounds, and of their solvates, any reference hereinbefore and hereinafter to the free compounds is to be understood as referring also to the corresponding salts, and the solvates thereof, for example hydrates, as appropriate and expedient.

The compounds of formula A, B, C, D, I, II, III, IV, V or VI especially those wherein $R_5$ is hydrogen, possess valuable pharmacological properties.

In the case of the groups of radicals or compounds mentioned hereinbefore and hereinafter, general definitions may, insofar as appropriate and expedient, be replaced by the more specific definitions stated hereinbefore and hereinafter.

Preference is given to a compounds of formula I, II, III, IV, V, VI wherein $R_1$ and $R_2$ independently of each other are lower alkyl, lower alkyl substituted by halogen, $C_6$-$C_{14}$aryl, hydroxy, lower alkoxy, phenyl-lower alkoxy, phenyloxy, lower alkanoyloxy, benzoyloxy, amino, lower alkylamino, lower alkanoylamino, phenyl-lower alkylamino, N,N-di-lower alkylamino, N,N-di-(phenyl-lower alkyl)amino, cyano, mercapto, lower alkylthio, carboxy, lower alkoxycarbonyl, carbamoyl, N-lower alkylcarbamoyl, N,N-di-lower alkylcarbamoyl, sulfo, lower alkanesulfonyl, lower alkoxysulfonyl, aminosulfonyl, N-lower-alkylaminosulfonyl or N,N-di-lower alkylaminosulfonyl; halogen; lower alkoxy; $C_6$-$C_{14}$aryloxy; $C_6$-$C_{14}$aryl-lower alkoxy; lower alkanoyloxy; $C_6$-$C_{14}$arylcarbonyloxy; amino monosubstituted or disubstituted by lower alkyl, $C_6$-$C_{14}$aryl, $C_6$-$C_{14}$aryl-lower alkyl, lower alkanoyl or $C_6$-$C_{12}$arylcarbonyl; cyano; nitro; mercapto; lower alkylthio; $C_6$-$C_{14}$arylthio; $C_6$-$C_{14}$aryl-lower alkylthio; lower alkanoylthio; $C_6$-$C_{14}$aryl-lower alkanoylthio; carboxy; lower alkoxycarbonyl, $C_6$-$C_{14}$aryl-lower alkoxycarbonyl; $C_6$-$C_{14}$aryloxycarbonyl; carbamoyl; carbamoyl N-mono- or N,N-disubstituted by lower alkyl, $C_6$-$C_{14}$aryl or $C_6$-$C_{14}$aryl-lower alkyl; sulfo; $C_6$-$C_{14}$arylsulfonyl; $C_6$-$C_{14}$aryl-lower alkanesulfonyl; lower alkanesulfonyl; or aminosulfonyl N-mono- or N,N-disubstituted by lower alkyl, $C_6$-$C_{14}$aryl or $C_6$-$C_{14}$aryl-lower alkyl, wherein $C_6$-$C_{14}$aryl is an aryl radical with 6 to 12 carbon atoms in the ring system, which may be unsubstituted or substituted by halogen, phenyl or naphthyl, hydroxy, lower alkoxy, phenyl-lower alkoxy, phenyloxy, lower alkanoyloxy, benzoyloxy, amino, lower alkylamino, lower alkanoylamino, phenyl-lower alkylamino, N,N-di-lower alkylamino, N,N-di-(phenyl-lower alkyl)amino, cyano, mercapto, lower alkylthio, carboxy, lower alkoxycarbonyl, carbamoyl, N-lower alkylcarbamoyl, N,N-di-lower alkylcarbamoyl, sulfo, lower alkanesulfonyl, lower alkoxysulfonyl, aminosulfonyl, N-lower alkylaminosulfonyl or N,N-di-lower alkylaminosulfonyl;

n and m are independently of each other 0 or 1 or 2, preferably 0;

$R_3$, $R_4$, $R_8$, $R_{10}$ are independently of each other hydrogen, lower alkyl, lower alkenyl or lower alkadienyl, which are each unsubstituted or monosubstituted or polysubstituted, preferably monosubstituted or disubstituted by a substituent independently selected from lower alkyl; hydroxy; lower alkoxy, which may be unsubstituted or mono-, di-, or trisubstituted by (i) heterocyclyl with 4 to 12 ring atoms, which may be unsaturated, wholly saturated, or partly saturated, is monocyclic or bicyclic and may contain up to three heteroatoms selected from nitrogen, oxygen and sulfur, and is most especially pyrrolyl, for example 2-pyrrolyl or 3-pyrrolyl, pyridyl, for example 2-, 3- or 4-pyridyl, or in a broader sense also thienyl, for example 2- or 3-thienyl, or furyl, for example 2-furyl, indolyl, typically 2- or 3-indolyl, quinolyl, typically 2- or 4-quinolyl, isoquinolyl, typically 3- or 5-isoquinolyl, benzofuranyl, typically 2-benzofuranyl, chromenyl, typically 3-chromenyl, benzothienyl, typically 2- or 3-benzothienyl; imidazolyl, typically 1- or 2-imidazolyl, pyrimidinyl, typically 2-or 4-pyrimidinyl, oxazolyl, typically 2-oxazolyl, isoxazolyl, typically 3-isoxazolyl, thiazolyl, typically 2-thiazolyl, benzimidazolyl, typically 2-benzimidazolyl, benzoxazolyl, typically 2-benzoxazolyl, quinazolyl, typically 2-quinazolinyl, 2-tetrahydrofuryl, 4-tetrahydrofuryl, 4-tetrahydropyranyl, 1-, 2- or 3-pyrrolidyl, 1-, 2-, 3-, or 4-piperidyl, 1-, 2-or 3-morpholinyl, 2- or 3-thiomorpholinyl, 2-pipe bis-lower alkyl-2-piperazinyl, (ii) by halogen, (iii) by hydroxy or (iv) by lower alkoxy; phenoxy; phenyl-lower alkoxy; heterocyclyloxy, wherein heterocyclyl is pyrrolyl, for example 2-pyrrolyl or 3-pyrrolyl, pyridyl, for example 2-, 3- or 4-pyridyl, or in a broader sense also thienyl, for example 2- or 3-thienyl, or furyl, for example 2-furyl, indolyl, typically 2- or 3-indolyl, quinolyl, typically 2- or 4quinolyl, isoquinolyl, typically 3- or 5isoquinolyl, benzofuranyl, typically 2-benzofuranyl, chromenyl, typically 3-chromenyl, benzothienyl, typically 2- or 3-benzothienyl; imidazolyl, typically 1- or 2-imidazolyl, pyrimidinyl, typically 2-or 4-pyrimidinyl, oxazolyl, typically 2-oxazolyl, isoxazolyl, typically 3-isoxazolyl, thiazolyl, typically 2-thiazolyl, benzimid-azolyl, typically 2-benzimidazolyl, benzoxazolyl, typically 2-benzoxazolyl, quinazolyl, typically 2-quinazolinyl, 2-tetrahydrofuryl, 4-tetrahydrofuryl, 2- or 4-tetrahydropyranyl, 1-, 2- or 3-pyrrolidyl, 1-, 2-, 3-, or 4-piperidyl, 1-, 2-or 3-morpholinyl, 2- or 3-thiomorpholinyl, piperazinyl or N,N'-bis-lower alkyl-2-piperazinyl, such as especially 2- or 4-tetrahydropyranyloxy; lower alkanoyloxy; carboxy; lower alkoxycarbonyl; phenyl-lower alkoxycarbonyl; mercapto; lower alkylthio; phenylthio; halogen; halogen-lower alkyl; oxo (except in the 1-position, because otherwise acyl); azido; nitro; cyano; amino; mono-lower alkylamino; di-lower alkylamino; pyrrolidino; imidazol-1-yl; piperidino; piperazino; 4-lower alkylpiperazino; morpholino; thiomorpholino; diphenylamino or dibenzylamino unsubstituted or substituted in the phenyl part by lower alkyl, lower alkoxy, halogen and/or nitro; lower alkoxycarbonylamino; phenyl-lower alkoxycarbonylamino unsubstituted or substituted in the phenyl part by lower alkyl or lower alkoxy; fluorenylmethoxycarbonylamino; amino-lower alkyl; monosubstituted or disubstituted amino-lower alkyl, wherein the amino substituent is selected from lower alkyl, hydroxy-lower alkyl, $C_3$-$C_8$cycloalkyl, amino-lower alkyl, N-mono- or N,N-di(-lower alkyl)amino-lower alkyl, amino, N-mono- or N,N-di-lower alkylamino and N-mono- or N,N-di-(hydroxy-lower alkyl)amino; pyrrolidino-lower alkyl; piperidino-lower alkyl; piperazino-lower alkyl; 4-lower alkylpiperazino-lower alkyl; imidazol-1-yl-lower alkyl; morpholino-lower alkyl; thiomorpholino-lower alkyl; S-oxo-thiomorpholino-lower alkyl; S,S-dioxothiomorpholino-lower alkyl; lower alkylendioxy; sulfamoyl; sulfo; carbamoyl; ureido; guanidino; cyano; aminocarbonyl (carbamoyl) and aminocarbonyloxy, which are substituted by one or two radicals on the nitrogen, wherein the amino substituents are selected independently of one another from the group comprising lower alkyl, hydroxy-lower alkyl, $C_3$-$C_8$cycloalkyl, amino-lower alkyl, N-mono- or N,N-di(-lower alkyl)amino-lower alkyl, amino, N-mono- or N,N-di-lower alkylamino and N-mono- or N,N-di-(hydroxy-lower alkyl)amino; pyrrolidinocarbonyl; piperidinocarbonyl; piperazinocarbonyl; 4-lower alkylpiperazinocarbonyl; imidazolinocarbonyl; morpholinocarbonyl; thiomorpholinocarbonyl; S-oxo-thiomorpholinocarbonyl; and S,S-dioxothiomorpholino;

phenyl, naphthyl, phenyl-lower alkyl or phenyl-lower alkenyl with a terminal phenyl radical, which is unsubstituted or monosubstituted or disubstituted by the radicals named above as substituents of lower alkyl, lower alkenyl or lower alkadienyl;

or heterocyclyl-lower alkyl, wherein heterocyclyl is pyrrolyl, for example 2-pyrrolyl or 3-pyrrolyl, pyridyl, for example 2-, 3- or 4-pyridyl, or in a broader sense also thienyl, for example 2- or 3-thienyl, or furyl, for example 2-furyl, indolyl, typically 2- or 3-indolyl, quinolyl, typically 2- or 4quinolyl, isoquinolyl, typically 3- or 5-isoquinolyl, benzofuranyl, typically 2-benzofuranyl, chromenyl, typically 3-chromenyl, benzothienyl, typically 2- or 3-benzothienyl; imidazolyl, typically 1- or 2-imidazolyl, pyrimidinyl, typically 2-or 4pyrimidinyl, oxazolyl, typically 2-oxazolyl, isoxazolyl, typically 3-isoxazolyl, thiazolyl, typically 2-thiazolyl, benzimidazolyl, typically 2-benzimidazolyl, benzoxazolyl, typically 2-benzoxazolyl, quinazolyl, typically 2-quinazolinyl, 2-tetrahydrofuryl, 4-tetrahydrofuryl, 2- or 4-tetrahydropyranyl, 1-, 2- or 3-pyrrolidyl, 1-, 2-, 3-, or 4-piperidyl, 1-, 2-or 3-morpholinyl, 2- or 3-thiomorpholinyl, 2-piperazinyl or N,N'-bis-lower alkyl-2-piperazinyl, which in each case are unsubstituted or monosubstituted or disubstituted by the radicals named above as substituents of lower alkyl, lower alkenyl, or lower alkadienyl;

or acyl of the subformula Y—C(=W)—, wherein W is oxygen and Y is hydrogen, $R^o$, $R^o$—O—, $R^o$HN—, or $R^oR^oN$— (wherein the radicals $R^o$ may be the same or different), or acyl of the subformula $R^{o-SO}2$—, whereby $R_4$ may also be absent for the compound of formula II;

or $R_4$ is absent for compounds of formula II, hydrogen or $CH_3$ for compounds of formula I, and $R_3$ is acyl of the subformula Y—C(=W)—, wherein W is oxygen and Y is hydrogen, $R^o$, $R^o$—O—, $R^o$HN—, or $R^oR^oN$— (wherein the radicals $R^o$ may be the same or different), or is acyl of the subformula $R^o$—$SO_2$—, wherein $R^o$ in the said radicals has the following meanings: substituted or unsubstituted lower alkyl, especially methyl or ethyl, amino-lower alkyl hydroxy-lower alkyl, wherein the amino group is unprotected or is protected by a conventional amino protecting group—especially by lower alkoxycarbonyl, typically tert-lower alkoxycarbonyl, for example tert-butoxycarbonyl—e.g. aminomethyl, R,S-, R- or preferably S-1-aminoethyl, tert-butoxycarbonylaminomethyl or R,S-, R-, or preferably S-1-(tert-butoxycarbonylamino)ethyl, carboxy-lower alkyl, typically 2-carboxyethyl, lower alkoxycarbonyl-lower alkyl, typically 2-(tert-butoxycarbonyl)ethyl, cyano-lower alkyl, typically 2-cyanoethyl, tetrahydropyranyloxy-lower alkyl, typically 4-(tetrahydropyranyl)oxymethyl, morpholino-lower alkyl, typically 2-(morpholino)ethyl, phenyl, lower alkylphenyl, typically 4-methyl phenyl, lower alkoxyphenyl, typically 4-methoxyphenyl, imidazolyl-lower alkoxyphenyl, typically 4-[2-(imidazol-1-yl)ethyl)oxyphenyl, carboxyphenyl, typically 4-carboxyphenyl, lower alkoxycarbonylphenyl, typically 4-ethoxycarbonylphenyl or 4-methoxyphenyl, halogen-lower alkylphenyl, typically 4-chloromethylphenyl, pyrrolidinophenyl, typically 4-pyrrolidinophenyl, imidazol-1-ylphenyl, typically 4-(imidazolyl-1-yl)phenyl, piperazinophenyl, typically 4-piperazinophenyl, (4-lower alkylpiperazino)phenyl, typically 4-(4-methylpiperazino)phenyl, morpholinophenyl, typically 4-morpholinophenyl, pyrrolidino-lower alkylphenyl, typically 4-pyrrolidinomethylphenyl, imidazol-1-yl-lower alkylphenyl, typically 4-(imidazolyl-1-ylmethyl)phenyl, piperazino-lower alkylphenyl, typically 4-piperazinomethylphenyl, (4-lower alkylpiperazinomethyl)-phenyl, typically 4-(4-methylpiperazinomethyl)phenyl, morpholino-lower alkylphenyl, typically 4-morpholinomethylphenyl, piperazinocarbonylphenyl, typically 4-piperazinocarbonylphenyl, or (4-lower alkylpiperazino)phenyl, typically 4-(4-methylpiperazino)phenyl.

p is 0 if $R_4$ is absent, or is 1 if $R_3$ and $R_4$ are both present and in each case are one of the aforementioned radicals (for compounds of formula II);

$R_5$ is hydrogen or lower alkyl, especially hydrogen,

X stands for 2 hydrogen atoms, for 0, or for 1 hydrogen atom and hydroxy; or for 1 hydrogen atom and lower alkoxy;

Z is hydrogen or especially lower alkyl, most especially methyl;

and for compounds for formula II, either the two bonds characterised by wavy lines are preferably absent in ring A and replaced by 4 hydrogen atoms, and the two wavy lines in ring B each, together with the respective parallel bond, signify a double bond;

or also the two bonds characterised by wavy lines are absent in ring B and replaced by a total of 4 hydrogen atoms, and the two wavy lines in ring A each, together with the respective parallel bond, signify a double bond;

or both in ring A and in ring B all of the 4 wavy bonds are absent and are replaced by a total of 8 hydrogen atoms;

or a salt thereof, if at least one salt-forming group is present. Particular preference is given to a compound of formula I wherein;

m and n are each 0;

$R_3$ and $R_4$ are independently of each other hydrogen, lower alkyl unsubstituted or mono- or disubstituted, especially monosubstituted, by radicals selected independently of one another from carboxy; lower alkoxycarbonyl; and cyano;

or $R_4$ is hydrogen or —CH$_3$, and $R_3$ is as defined above or preferably $R_3$ is, acyl of the subformula R°—CO, wherein R° is lower alkyl; amino-lower alkyl, wherein the amino group is present in unprotected form or is protected by lower alkoxycarbonyl; tetrahydropyranyloxy-lower alkyl; phenyl; imidazolyl-lower alkoxyphenyl; carboxyphenyl; lower alkoxycarbonylphenyl; halogen-lower alkylphenyl; imidazol-1-ylphenyl; pyrrolidino-lower alkylphenyl; piperazino-lower alkylphenyl; (4-lower alkylpiperazinomethyl)phenyl; morpholino-lower alkylphenyl; piperazinocarbonylphenyl; or (4-lower alkylpiperazino)phenyl;

or is acyl of the subformula R°—CO—, wherein R° is lower alkyl;

or is acyl of the subformula R°HN—C(=W)—, wherein W is oxygen and R° has the following meanings: morpholino-lower alkyl, phenyl, lower alkoxyphenyl, carboxyphenyl, or lower alkoxycarbonylphenyl;

or $R_3$ is lower alkylphenylsulfonyl, typically 4-toluenesulfonyl;

further specific examples of preferred $R_3$ groups are described below for the preferred compounds of formula II, $R_5$ is hydrogen or lower alkyl, especially hydrogen, X stands for 2 hydrogen atoms or for O;

Z is methyl or hydrogen;

or a salt thereof, if at least one salt-forming group is present. Particular preference is given to a compound of formula II wherein m and n are each 0;

$R_3$ and $R_4$ are independently of each other hydrogen, lower alkyl unsubstituted or mono- or disubstituted, especially monosubstituted, by radicals selected independently of one another from carboxy; lower alkoxycarbonyl; and cyano; whereby $R_4$ may also be absent;

or $R_4$ is absent, and $R_3$ is acyl from the subformula R°—CO, wherein R° is lower alkyl, especially methyl or ethyl;

amino-lower alkyl, wherein the amino group is unprotected or protected by lower alkoxy-carbonyl, typically tert-lower alkoxycarbonyl, for example tert-butoxycarbonyl, e.g. aminomethyl, R,S-, R-, or preferably S-1-aminoethyl, tert-butoxycarbonylaminomethyl or R,S-, R-, or preferably S1-(tert-butoxycarbonylamino)ethyl; tetrahydropyranyloxy-lower alkyl, typically 4-(tetrahydropyranyl)oxymethyl; phenyl; imidazolyl-lower alkoxyphenyl, typically 4-[2-(imidazol-1-yl)ethyl)oyxphenyl; carboxyphenyl, typically 4-carboxyphenyl; lower alkoxycarbonylphenyl, typically 4-methoxy- or 4-ethoxycarbonylphenyl; halogen-lower alkylphenyl, typically 4-chloromethylphenyl; imidazol-1-ylphenyl, typically 4-(imidazolyl-1-yl)-phenyl; pyrrolidino-lower alkylphenyl, typically 4-pyrrolidinomethylphenyl; piperazino-lower alkylphenyl, typically 4-piperazinomethylphenyl; (4-lower alkylpiperazinomethyl)phenyl, typically 4-(4-methylpiperazinomethyl)phenyl; morpholino-lower alkylphenyl, typically 4-morpholinomethylphenyl; piperazinocarbonylphenyl, typically 4-piperazinocarbonylphenyl; or (4-lower alkylpiperazino)phenyl, typically 4-(4-methylpiperazino)phenyl;

or is acyl of the subformula R°—O—CO—, wherein R° is lower alkyl; or is acyl of the subformula R° HN—C(=W)—, wherein W is oxygen and R° has the following preferred meanings: morpholino-lower alkyl, typically 2-morpholinoethyl, phenyl, lower alkoxyphenyl, typically 4-methoxyphenyl or 4-ethoxyphenyl, carboxyphenyl, typically 4-carboxyphenyl, or lower alkoxycarbonylphenyl, typically 4-ethoxycarbonylphenyl;

or is lower alkylphenylsulfonyl, typically 4-toluenesulfonyl;

p is 0 if $R_4$ is absent, or is 1 if $R_3$ and $R_4$ are both present and in each case are one of the aforementioned radicals;

$R_5$ is hydrogen or lower alkyl, especially hydrogen,

X stands for 2 hydrogen atoms or for O;

Z is methyl or hydrogen;

and either the two bonds characterised by wavy lines are preferably absent in ring A and replaced by 4 hydrogen atoms, and the two wavy lines in ring B each, together with the respective parallel bond, signify a double bond;

or also the two bonds characterised by wavy lines are absent in ring B and replaced by a total of 4 hydrogen atoms, and the two wavy lines in ring A each, together with the respective parallel bond, signify a double bond;

or both in ring A and in ring B all of the 4 wavy bonds are absent and are replaced by a total of 8 hydrogen atoms;

or a salt thereof, if at least one salt-forming group is present.

Most especially preferred compounds of formula II are selected from;

8,9,10,11-Tetrahydrostaurosporine;
N-[4-(4-methylpiperaziN-1-ylmethyl)benzoyl]-1,2,3,4-tetrahydrostaurosporine;
N-(4-chloromethylbenzoyl)-1,2,3,4-tetrahydrostaurosporine;
N-(4-(pyrrolidin-1-ylmethyl)benzoyl)1,2,3,4-tetrahydrostaurosporine;
N-(4-(morpholin-4-ylmethyl)benzoyl)1,2,3,4-tetrahydrostaurosporine;
N-(4-(piperazin-1-ylmethyl)benzoyl)-1,2,3,4-tetrahydrostaurosporine;
N-ethyl-1,2,3,4-tetrahydrostaurosporine;
N-tosyl-1,2,3,4-tetrahydrostaurosporine;
N-triflouroacetyl-1,2,3,4-tetrahydrostaurosporine;
N-[4-(2-imidazol-1-yl-ethoxy)benzoyl]-1,2,3,4-tetrahydrostaurosporine;
N-methoxycarbonylmethyl-1,2,3,4-tetrahydrostaurosporine;
N-carboxymethyl-1,2,3,4-tetrahydrostaurosporine;
N-terephthaloylmethyl ester-1,2,3,4-tetrahydrostaurosporine;
N-terephthaloyl-1,2,3,4-tetrahydrostaurosporine;
N-(4-ethylpiperazinylcarbonylbenzoyl)-1,2,3,4-tetrahydrostaurosporine;
N-(2-cyanoethyl)-1,2,3,4-tetrahydrostaurosporine;
N-benzoyl-1,2,3,4-tetrahydrostaurosporine;
N,N-dimethyl-1,2,3,4-tetrahydrostaurosporinium iodide;
N-BOC-glycyl-1,2,3,4-tetrahydrostaurosporine;
N-glycyl-1,2,3,4-tetrahydrostaurosporine;
N-(3-(tert-butoxycarbonyl)propyl)-1,2,3,4-tetrahydrostaurosporine;
N-(3-carboxypropyl)-1,2,3,4-tetrahydrostaurosporine;

N-(4-imidazol-1-yl)benzoyl]-1,2,3,4-tetrahydrostaurosporine;
N-[(tetrahydro-2h-pyran-4-yloxy)acetyl]-1,2,3,4-tetrahydrostaurosporine;
N-BOC-l-alanyl-1,2,3,4-tetrahydrostaurosporine;
N-l-alanyl-1,2,3,4-tetrahydrostaurosporine hydrochloride;
N-methyl-1,2,3,4-tetrahydro-6-methylstaurosporine;
N-(4-carboxyphenylaminocarbonyl)-1,2,3,4-tetrahydrostaurosporine;
N-(4-ethylphenylaminocarbonyl)-1,2,3,4-tetrahydrostaurosporine;
N-(N-phenylaminocarbonyl)-1,2,3,4-tetrahydrostaurosporine;
N-(N-[2-(1-morpholino)ethyl]aminocarbonyl)-1,2,3,4-tetrahydrostaurosporine;
N-(N-[4methoxyphenyl]aminocarbonyl)-1,2,3,4-tetrahydrostaurosporine;
1,2,3,4-tetrahydro-6-methylstaurosporine;
N-BOC-1,2,3,4-tetrahydrostaurosporine;
N-BOC-1,2,3,4-tetrahydro-6-methylstaurosporine;
N-BOC-1,2,3,4-tetrahydro-6-methyl-7-oxo-staurosporine;
1,2,3,4,8,9,10,11-octahydrostaurosporine;
or a pharmaceutically acceptable salt thereof, if at least one salt-forming group is present.

Most especially preferred is the compound of formula I designated 1,2,3,4-tetrahydrostaurosporine, or a (particularly pharmaceutically acceptable) salt thereof (here, m und n in formula I are 0, $R_3$ is hydrogen, $R_4$ is absent, provided no salt is present (p=0), or is hydrogen if a salt is present (p=1), $R_5$ is hydrogen, the two bonds represented by wavy lines are absent in Ring A and are replaced by a total of 4 hydrogen atoms and the two bonds represented by wavy lines in Ring B are in each case a double bond together with the parallel bonds, X stands for 2 hydrogen atoms, and Z is methyl).

Most especially preferred are the compounds of formula A wherein;
A) X=O; $R_1$, $R_2$, $R_5$=H; Q=—$(CH_2)_2$—O—$CH(CH_2)$OH—$(CH_2)_2$—(LY 333531)
B) X=O; $R_1$, $R_2$, $R_5$=H; Q=—$(CH_2)_2$—O—$CH(CH_2N(CH_3)_2)$—$(CH_2)_2$—
C) X=2 hydrogen atoms; $R_1$, $R_2$, $R_5$=H;

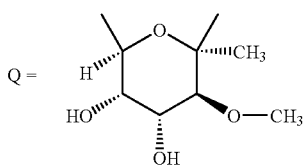

(MLR52; CAS=155416-34-5)

Most especially preferred are the compounds of formula I wherein;
A) X=2 hydrogen atoms; $R_1$,$R_2$, $R_3$, $R_5$=H; $R_4$=$CH_3$; Z=$CH_3$ (staurosporine)
B) X=1 hydrogen and 1 hydroxy atoms in (R) or (S) isomeric form; $R_1$,$R_2$, $R_3$,$R_5$=H; $R_4$=$CH_3$; Z=$CH_3$ (UCN-01 and UCN-02)
C) X=2 hydrogen atoms; $R_1$,$R_2$, $R_5$=H; $R_4$=$CH_3$; $R_3$,=benzoyl; Z=$CH_3$ (CGP41251 or PKC412 or MIDOSTAURIN)
D) X=O; $R_1$,$R_2$, $R_5$=H; $R_3$=$CH_3$; $R_4$=ethyloxycarbonyl; Z=$CH_3$ (NA 382; CAS=143086-33-3).
E) X=1 hydrogen and 1 hydroxy atom; $R_1$, $R_2$, $R_5$=H; $R_3$=$CH_3$; Z=$CH_3$; and $R_4$ is selected from —$(CH_2)_2$OH; —$CH_2CH(OH)CH_2OH$; —$CO(CH_2)_2CO_2Na$; —$(CH_2)_3CO_2H$; —$COCH_2N(CH_3)_2$;

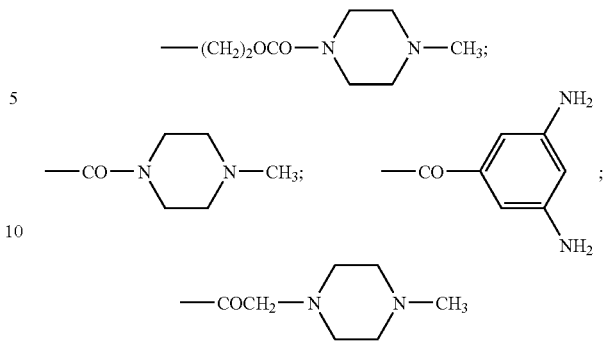

F) X=2 hydrogen atoms; $R_1$, $R_2$, $R_5$=H; $R_3$=$CH_3$; Z=$CH_3$; and $R_4$ is selected from N-[0-(tetrahydropyran-4-yl)-D-lactoyl]; N-[2-methyl-2-(tetrahydropyran-4-yloxy)-propionyl; N-[0-(tetrahydropyran-4-yl)-L-lactoyl]; N-[0-(tetrahydropyran-4-yl)-D-lactoyl]; N-[2-(tetrahydro-pyran-4-yloxy)-acetyl)]
G) X=O; $R_1$, $R_2$, $R_5$=H; $R_3$=$CH_3$; Z=$CH_3$; and $R_4$ is selected from N-[0-(tetrahydropyran-4-yl)-D-lactoyl]; N-[2-(tetrahydro-pyran-4-yloxy)-acetyl)]
H) X=1 hydrogen and 1 hydroxy atom; $R_1$, $R_2$, $R_5$=H; $R_3$=$CH_3$;Z=$CH_3$; and $R_4$ is selected from N-[0-(tetrahydropyran-4-yl)-D-lactoyl]; N-[2-(tetrahydro-pyran-4-yloxy)-acetyl)]

The abbreviation "CAS" means the CHEMICAL ABSTRACTS registry number.

The most preferred compounds of formula I e.g. MIDOSTAURIN [International Nonproprietary Name] are covered and have been specifically described by the European patent No. 0 296 110 published on Dec. 21, 1988, as well as in U.S. Pat. No. 5,093,330 published on Mar. 3, 1992, and Japanese Patent No. 2 708 047 all in the name of the applicant. Other preferred compounds are covered and described by the patent applications WO 95/32974 and WO 95/32976 both published on Dec. 7, 1995, in the name of the applicant. All the compounds described in these documents are incorporated into the present application by reference.

Most especially preferred are the compounds of formula III wherein;
A) X=2 hydrogen atoms; $R_1$,$R_2$, $R_5$=H; $R_6$=$CH_3$; $R_7$=methyloxycarbonyl; Z=H (2-methyl K252a)
B) X=2 hydrogen atoms; $R_1$,$R_2$, $R_5$, $R_6$=H; $R_7$=methyloxycarbonyl; Z=H (K-252a)
C) X=2 hydrogen atoms; $R_1$,$R_2$, $R_5$, $R_6$=H; $R_7$=methyloxycarbonyl; Z=$CH_3$ (KT-5720)

Most especially preferred are the compounds of formula IV wherein;
A) X=O; $R_1$, $R_2$, $R_5$=H; $R_9$=$CH_2$—$NMe_2$; $R_8$=$CH_3$; m'=n'=2
B) X=O; $R_1$, $R_2$, $R_5$=H; $R_9$=$CH_2$—$NH_2$; $R_8$=$CH_3$; m'=2; n'=1 (Ro-31-8425; CAS=151342-35-7)

Most especially preferred are the compounds of formula V wherein;
A) X=O; $R_1$, $R_2$, $R_5$=H; $R_8$=$CH_3$; $R_{10}$=—$(CH_2)_3$—$NH_2$; (Ro-31-7549; CAS=138516-31)
B) X=O; $R_1$, $R_2$, $R_5$=H; $R_8$=$CH_3$; $R_{10}$=—$(CH_2)_3$—S—(C=NH)—$NH_2$; (Ro-31-8220; CAS=125314-64-9))
C) X=O; $R_1$, $R_2$, $R_5$=H; $R_8$=$CH_3$; $R_{10}$=—$CH_3$;

Most especially preferred are the compounds of formula VI wherein;
A) X=2 hydrogen atoms; $R_1$,$R_2$, $R_5$=H; $R_4$=$CH_3$; Z=$CH_3$; $R_3$ selected from methyl or ($C_1$-$C_{10}$)alkyl, arylmethyl, $C_6H_2CH_2$—

STAUROSPORINE DERIVATIVES and their manufacturing process have been specifically described in many prior art documents, well known by the man skilled in the art.

Compounds of formula A, B, C, D and their manufacturing process have for instance, been described in the European patents No. 0 657 458 published on Jun. 14, 1995, in the European patents No. 0 624 586 published on Nov. 17, 1994, in the European patents No. 0 470 490 published on Feb. 12, 1992, in the European patents No. 0 328 026 published on Aug. 16, 1989, in the European patents No. 0 384 349 published on Aug. 29, 1990, as well as in many publications such as Barry M. Trost* and *Weiping Tang* Org. Lett., 3(21), 3409-3411.

Compounds of formula I and their manufacturing process has been specifically described in the European patents No. 0 296 110 published on Dec. 21, 1988, as well as in U.S. Pat. No. 5,093,330 published on Mar. 3, 1992, and Japanese Patent No. 2 708 047 all in the name of the applicant. Compounds of formula I having a tetrahydropyran-4-yl)-lactoyl substitution on $R_4$ have been described in the European patent No. 0 624 590 published on Nov. 17, 1994. Other compounds have been described in the European patent No. 0 575 955 published Dec. 29, 1993, European patent No. 0 238 011 published on Sep. 23, 1987 (UCN-O1), International patent application EP98/04141 published as WO99/02532 on Jul. 3, 1998.

Compounds of formula II and their manufacturing process has been specifically described in the European patents No. 0 296 110 published on Dec. 21, 1988, as well as in U.S. Pat. No. 5,093,330 published on Mar. 3, 1992, and Japanese Patent No. 2 708 047 all in the name of the applicant.

Compounds of formula III and their manufacturing process has been specifically described in the patent applications claiming the priority of the U.S. patent application US 920102 filed on Jul. 24, 1992. (i.e European patents No. 0 768 312 published on Apr. 16, 1997, No. 1 002 534 published May 24, 2000, No. 0 651 754 published on May 10, 1995.

Compounds of formula IV and their manufacturing process has been specifically described in the patent applications claiming the priority of the British patent applications GB 9309602 and GB 9403249 respectively filed on May 10, 1993, and on Feb. 21, 1994. (i.e European patents No. 0 624 586 published on Nov. 17, 1994, No. 1 002 534 published May 24, 2000, No. 0 651 754 published on May 10, 1995.

Compounds of formula V and their manufacturing process has been specifically described in the patent applications claiming the priority of the British patent applications GB 8803048, GB 8827565, GB 8904161 and GB 8928210 respectively filed on Feb. 10, 1988, Nov. 25, 1988, Feb. 23, 1989 and Dec. 13, 1989. (i.e European patents No. 0 328 026 published on Aug. 16, 1989, and No. 0 384 349 published Aug. 29, 1990).

Compounds of formula VI and their manufacturing process has been specifically described in the patent applications claiming the priority of the U.S. patent applications Ser. No. 07/777,395 (Con), filed on Oct. 10, 1991 (i.e International patent application WO 93/07153 published on Apr. 15, 1993).

In each case where citations of patent applications or scientific publications are given in particular for the STAUROSPORINE DERIVATIVE compounds, the subject-matter of the final products, the pharmaceutical preparations and the claims is hereby incorporated into the present application by reference to this publications.

The structure of the active agents identified by code nos., generic or trade names may be taken from the actual edition of the standard compendium "The Merck Index" or from data bases, e.g. Patents International (e.g. IMS World Publications). The corresponding content thereof is hereby incorporated by reference.

The preferred STAUROSPORINE DERIVATIVE according to the invention is N-[(9S,10R,11R,13R)-2,3,10,11,12,13-hexahydro-10-methoxy-9-methyl-1-oxo-9,13-epoxy-1H,9H-diindolo[1,2,3-gh:3',2',1'-lm]pyrrolo[3,4-j][1,7]benzodiazonin-11-yl]—N—methylbenzamide of the formula (VII):

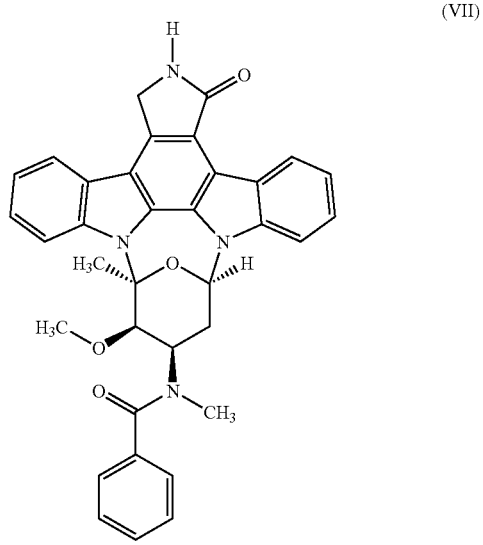

(VII)

or a salt thereof, (hereinafter: "Compound of formula VII or MIDOSTAURIN").

Compound of formula VII is also known as MIDOSTAURIN [International Nonproprietary Name] or PKC412.

MIDOSTAURIN is a derivative of the naturally occurring alkaloid staurosporine, and has been specifically described in the European patent No. 0 296 110 published on Dec. 21, 1988, as well as in U.S. Pat. No. 5,093,330 published on Mar. 3, 1992, and Japanese Patent No. 2 708 047 all in the name of the applicant.

It has now surprisingly been found that MIDOSTAURIN possesses therapeutic properties, which render it particularly useful as an inhibitor of FLT3 receptors and especially in the treatment and prophylaxis of leukemias and myelodysplastic syndromes. This compound shows an unexpected high potency toward the FLT3 receptor kinase.

STAUROSPORINE DERIVATIVES e.g. MIDOSTAURIN were originally identified as inhibitor of protein kinase C (PKC) (Meyer T, Regenass U, Fabbro D, et al: Int J Cancer 43: 851-856, 1989).

It has now surprisingly been found that STAUROSPORINE DERIVATIVES possess therapeutic properties, which render it particularly useful as an inhibitor of FLT3 receptors and especially in the treatment and prophylaxis of leukemias and myelodysplastic syndromes. This compound shows an unexpected high potency toward the FLT3 receptor kinase.

The present invention thus concerns the use of STAUROSPORINE DERIVATIVES for the preparation of a drug for inhibiting FLT3 receptor kinase and downstream effects (mediated by SH2).

The present invention more particularly concerns the use of STAUROSPORINE DERIVATIVES for the preparation of a drug for the treatment of diseases involving deregulated FLT3 receptor tyrosine kinase activity more particularly deregulated mutant FLT3 receptor tyrosine kinase activity. Prefered diseases involving deregulated FLT3 receptor tyrosine kinase activity are leukemias and myelodysplastic syndrome.

The present invention more particularly concerns the use of STAUROSPORINE DERIVATIVES for the preparation of a drug for the treatment of leukemias and myelodysplastic syndrome. Most preferably for the treatment of leukemias and myelodysplastic syndrome involving deregulated FLT3 receptor tyrosine kinase activity.

In a preferred embodiment, the present invention concerns the use of STAUROSPORINE DERIVATIVES for the preparation of a drug for the treatment of acute myeloblastic leukemia and high risk myelodysplastic syndromes. Most preferably for the treatment of acute myeloblastic leukemia and high risk myelodysplastic syndromes involving deregulated FLT3 receptor tyrosine kinase activity In still another embodiment, the instant invention provides a method for treating diseases involving deregulated FLT3 receptor tyrosine kinase activity comprising administering to a mammal in need of such treatment a therapeutically effective amount of STAUROSPORINE DERIVATIVES, or a pharmaceutically acceptable salts or prodrugs thereof.

Preferably the instant invention provides a method for treating mammals especially humans suffering from diseases involving deregulated FLT3 receptor tyrosine kinase activity comprising administering to a mammal in need of such treatment a FLT3 receptor tyrosine kinase activity inhibiting amount of N-[(9S,10R,11R,13R)-2,3,10,11,12,13-hexahydro-10-methoxy-9methyl-1oxo-9,13-epoxy-1H,9H-diindolo[1,2,3-gh:3',2',1'-lm]pyrrolo[3,4-j][1,7]benzodiazonin-11-yl]-N-methylbenzamide of the formula (VII).

The instant invention also concerns a method wherein the therapeutically effective amount of the compound of formula VII is administered to a mammal subject 7 to 4 times a week or about 100% to about 50% of the days in the time period, for a period of from one to six weeks, followed by a period of one to three weeks, wherein the agent is not administered and this cycle being repeated for from 1 to several cycles.

Preferably, this method is used for treating leukemias and myelodysplastic syndromes.

More preferably, this method is used for treating acute myeloblastic leukemia and high risk myelodysplastic syndromes.

In another embodiment, the instant invention relates to the use of STAUROSPORINE DERIVATIVES for the preparation of a pharmaceutical composition for use in treating diseases involving deregulated FLT3 receptor tyrosine kinase activity more particularly deregulated mutant FLT3 receptor tyrosine kinase activity.

STAUROSPORINE DERIVATIVES have useful pharmacological properties. In particular, it inhibits the activity of FLT3 receptor tyrosine kinase activity in concentrations in the range of 0.01 to 1.0 μM.

In vivo, the activity of the STAUROSPORINE DERIVATIVES especially compounds of formula I or II, can be demonstrated, for example, in a single oral administration per day to animals at doses in the range of 5 to 300 or 100 to 200 mg/kg of body weight per day.

The STAUROSPORINE DERIVATIVES are therefore very highly suitable for the treatment of diseases, which respond to inhibition of the deregulated activity of FLT3 tyrosine kinase receptors, e.g. leukemias and myelodysplastic syndrome.

FLT3 is a member of the type III receptor tyrosine kinase (RTK) family. FLT3 (fms-like tyrosine kinase) is also known as FLk-2 (fetal liver kinase 2).

Aberrant expression of the FLT3 gene has been documented in both adult and childhood leukemias including acute myeloid leukemia (AML), AML with trilineage myelodysplasia (AMLUTMDS), acute lymphoblastic leukemia (ALL), and myelodysplastic syndrome (MDS).

Activating mutations of the FLT3 receptor have been found in about 35% of patients with acute myeloblastic leukemia (AML), and are associated with a poor prognosis. The most common mutation involves an in-frame duplication within the juxtamembrane domain, with an additional 5-10% of patients having a point mutation at asparagine 835. Both of these mutations are associated with constitutive activation of the tyrosine kinase activity of FLT3, and result in proliferation and viability signals in the absence of ligand. Patients expressing the mutant form of the receptor have been shown to have a decreased chance for cure. Thus, there is accumulating evidence for a role for hyperactivated (mutated) FLT3 kinase activity in human leukemias and myelodysplastic syndrome.

This has prompted the applicant to search for new inhibitors of the FLT3 receptor as a possible therapeutic approach in these patients, for whom current drug therapies offer little utility, and for such patients who have previously failed current available drug therapies and/or stem cell transplantation therapies.

The term "diseases involving deregulated FLT3 receptor tyrosine kinase activity" as used herein includes, but is not limited to, leukemias including acute myeloid leukemia (AML), AML with trilineage myelodysplasia (AML/TMDS), acute lymphoblastic leukemia (ALL), and myelodysplastic syndrome (MDS). This term also, specifically includes diseases resulting from FLT3 receptor mutation.

Leukemias generally result from an acquired (not inherited) genetic injury to the DNA of immature haematopoietic cells in the bone marrow, lymph nodes, spleen, or other organs of the blood and immune system. The effects are: the accelerated growth and blockage in the maturation of cells, resulting in the accumulation of cells called "leukemic blasts," which do not function as normal blood cells; and a failure to produce normal marrow cells, leading to a deficiency of red cells (anemia), platelets and normal white cells. Blast cells are normally produced by bone marrow and usually develop into mature blood cells, comprising about 1 percent of all marrow cells. In leukemia, the blasts do not mature properly and accumulate in the bone marrow. In acute meyloid leukemia (AML), these are called myeloblasts while in acute lymphoblastic leukemia (ALL) they are known as lymphoblasts.

Another leukemia is MLL (mixed-lieage leukemia).

The term "AML with trilineage myelodysplasia (AML/TMDS)" relates to an uncommon form of leukemia characterized by a dyshematopoietic picture accompanying the acute leukemia, a poor response to induction chemotherapy, and a tendency to relapse with pure myelodysplastic syndrome.

The term "Myelodysplastic Syndrome (MDS)" relates to a group of blood disorders in which the bone marrow stops functioning normally, resulting in a deficiency in the number of healthy blood cells. Compared with leukemia, in which one type of blood cell is produced in large numbers, any and sometimes all types of blood cells are affected in MDS. At least 10,000 new cases occur annually in the United States. Up to one third of patients diagnosed with MDS go on to develop acute myeloid leukemia. For this reason the disease is sometimes referred to as preleukemia. Myelodysplastic syndrome is sometimes also called myelodysplasia dysmyelopoiesis or oligoblastic leukemia. MDS is also referred to as smoldering leukemia when high numbers of blast cells remain in the marrow. Myelodysplastic syndrome results, like leukemia, from a genetic injury to the DNA of a single cell in the bone marrow. Certain abnormalities in chromosomes are present in MDS patients. These abnormalities are called translocations, which occur when a part of one chromosome breaks off and becomes attached to a broken part of a different chromosome. The same defects are frequently found in acute myeloid leukemia. MDS differs from leukemia because all of the patient's blood cells are abnormal and all are derived from the same damaged stem cell. In leukemia patients, the bone marrow contains a mixture of diseased and healthy blood cells.

AML and advanced myelodysplastic syndromes are currently treated with high doses of cytotoxic chemotherapy drugs such cytosine arabinoside and daunorubicin. This type of treatment induces about 70% of patients to enter a hematologic remission. However, more than half of the patients that enter remission will later relapse despite administration of chemotherapy over long periods of time. Almost all of the patients who either fail to enter remission initially, or relapse later after obtaining remission, will ultimately die because of leukemia. Bone marrow transplantation can cure up to 50-60% of patients who undergo the procedure, but only about one third of all patients with AML or MDS are eligible to receive a transplant. New and effective drugs are urgently needed to treat the patients who fail to enter remission with standard therapies, patients who later relapse, and patients that are not eligible for stem cell transplantation. Further, an effective new drug could be added to standard therapy with the reasonable expectation that it will result in improved induction chemotherapy for all patients.

In the present description, the term "treatment" includes both prophylactic or preventative treatment as well as curative or disease suppressive treatment, including treatment of patients at risk of contracting the disease or suspected to have contracted the disease as well as ill patients. This term further includes the treatment for the delay of progression of the disease.

The term "curative" as used herein means efficacy in treating ongoing episodes involving deregulated FLT3 receptor tyrosine kinase activity.

The term "prophylactic" means the prevention of the onset or recurrence of diseases involving deregulated FLT3 receptor tyrosine kinase activity.

The term "delay of progression" as used herein means administration of the active compound to patients being in a pre-stage or in an early phase of the disease to be treated, in which patients for example a pre-form of the corresponding disease is diagnosed or which patients are in a condition, e.g. during a medical treatment or a condition resulting from an accident, under which it is likely that a corresponding disease will develop.

To search for FLT3-targeted compounds, the applicant screened the inhibitory effects of several compounds on two different kinds of assays.

Tyrosine protein kinase assays with purified GST-Flt-3 were carried in a final volume of 30 µL containing 200-1800 ng of enzyme protein. The activity was assayed in the presence or absence of inhibitors, by measuring the incorporation of $^{33}P$ from $[\gamma^{33}P]$ ATP into appropriate substrates. In this assay MIDOSTAURIN inhibits the transfer of the gamma phosphate of ATP onto OH of Tyrosines in the protein substrate by the Flt-3 kinase in the range of 0.1 to 1.0 mM.

A cell based assay is utilised to identify inhibitors of mutant FLT3 tyrosine kinase receptors. The general technique involves comparing the effects of possible inhibitors on cell lines that depended on mutant FLT3 for proliferation, versus cell lines that do not depend on mutant FLT3 for proliferation. Cell lines expressing two different forms of mutated, activated FLT3 are used: Ba/F3-FLT3-ITD cells expressing a FLT3 mutant with an "Internal Tandem Duplication" (ITD) within the juxtamembrane domain of the receptor. Ba/F3-FLT3-D835Y cells expressing an FLT3 receptor containing a mutation converting Asparagine at position 835 to T-yrosine. MIDOSTAURIN, inhibited proliferation of both Ba/F3-FLT3-ITD and Ba/F3-D835Y cells at an $IC_{50}$ of <10 nM. MIDOSTAURIN did not inhibit growth of untransformed Ba/F3 cells at concentrations of up to 500 nM, and the growth inhibitory effects of COMPOUND I on Ba/F3-FLT3-ITD cells could be reversed by the addition of high concentrations of IL-3 to provide an alternative viability signal. At the concentrations required to inhibit the proliferation of FLT3-dependent cell-lines, MIDOSTAURIN was not cytotoxic against several human leukemia and lymphoma cell lines that did not have mutant FLT3 receptors (hyperactivated kinases), suggesting that the drug has an unexpected high degree of specificity as a cytoxic agent. Overall, these results indicate that MIDOSTAURIN is a potent inhibitor of mutant FLT3 receptor tyrosine kinase activity and is a promising candidate for testing as an anti-leukemia agent in patients with mutant FLT3 receptors. In particular, it inhibits the activity of FLT3 receptor tyrosine kinase activity in concentrations in the range of 0.01 to 1.0 µM.

This unforeseeable range of properties means that the use of STAUROSPORINE DERIVATIVES are of particular interest for the manufacture of a medicament for the treatment of diseases involving deregulated FLT3 receptor tyrosine kinase activity. This compound has a high safety margin, high affinity and selectivity.

This effect can especially be clinically relevant for patients with leukemias, especially Acute myeloid leukemia (AML) and myelodysplastic syndrome (MDS).

To demonstrate that STAUROSPORINE DERIVATIVES are particularly suitable for the treatment of leukemias or myelodysplastic syndromes with good therapeutic margin and other advantages, clinical trials can be carried out in a manner known to the skilled person.

The precise dosage of STAUROSPORINE DERIVATIVES to be employed for inhibiting FLT3 receptor tyrosine kinase activity depends upon several factors including the host, the nature and the severity of the condition being treated, the mode of administration. However, in general, satisfactory inhibition the FLT3 receptor tyrosine kinase activity is achieved when the STAUROSPORINE DERIVATIVES is administered (check preferred administration) parenterally, e.g., intraperitoneally, intravenously, intramuscularly, subcutaneously, intratumorally, or rectally, or enterally, e.g., orally, preferably intravenously or orally, intravenously at a daily dosage of 1-300 mg/kg body weight or, for most larger primates, a daily dosage of 50-5000, preferably 500-3000 mg, in human trials a total dose of 225 mg/day was most presumably the Maximum Tolerated Dose (MTD). A preferred intravenous daily dosage is 1-75 mg/kg body weight or, for most larger primates, a daily dosage of 50-1500 mg. A typical intravenous dosage is 20 mg/kg, three to five times a week.

Most preferably, the STAUROSPORINE DERIVATIVES, especially MIDOSTAURIN, are administered orally, by dosage forms such as microemulsions, soft gels or solid dispersions in dosages up to 150 mg/day, administered in one, two or three times.

Usually, a small dose is administered initially and the dosage is gradually increased until the optimal dosage for the host under treatment is determined. The upper limit of dosage is that imposed by side effects and can be determined by trial for the host being treated.

The STAUROSPORINE DERIVATIVES may be combined with one or more pharmaceutically acceptable carriers and, optionally, one or more other conventional pharmaceutical adjuvants and administered enterally, e.g. orally, in the form of tablets, capsules, caplets, etc. or parenterally, e.g., intraperitoneally or intravenously, in the form of sterile injectable solutions or suspensions. The enteral and parenteral compositions may be prepared by conventional means.

The infusion solutions according to the present invention are preferably sterile. This may be readily accomplished, e.g. by filtration through sterile filtration membranes. Aseptic formation of any composition in liquid form, the aseptic filling of vials and/or combining a pharmaceutical composition of the present invention with a suitable diluent under aseptic conditions are well known to the skilled addressee.

The STAUROSPORINE DERIVATIVES may be formulated into enteral and parenteral pharmaceutical compositions containing an amount of the active substance that is effective for inhibiting FLT3 receptor tyrosine kinase activity, such compositions in unit dosage form and such compositions comprising a pharmaceutically acceptable carrier.

The STAUROSPORINE DERIVATIVES can be used alone or combined with at least one other pharmaceutically active compound for use in these pathologies. These active compounds can be combined in the same pharmaceutical preparation or in the form of combined preparations "kit of parts" in the sense that the combination partners can be dosed independently or by use of different fixed combinations with distinguished amounts of the combination partners, i.e., simultaneously or at different time points. The parts of the kit of parts can then, e.g., be administered simultaneously or chronologically staggered, that is at different time points and with equal or different time intervals for any part of the kit of parts. Non-limiting examples of compounds which can be cited for use in combination with STAUROSPORINE DERIVATIVES are cytotoxic chemotherapy drugs, such as cytosine arabinoside, daunorubicin, doxorubicin, cyclophosphamide, VP-16, etc. Further, STAUROSPORINE DERIVATIVES could be combined with other inhibitors of signal transduction or other oncogene-targeted drugs with the expectation that significant synergy would result.

Examples of useful compositions are described in the European patents No. 0 296 110, No. 0 657 164, No. 0 296 110, No.0 733 372, No.0 711 556, No.0 711 557, all in the name of the applicant.

The preferred compositions are described in the European patent No. 0 657 164 published on Jun. 14, 1995. The described pharmaceutical compositions comprise a solution or dispersion of compounds of formula I such as MIDOSTAURIN in a saturated polyalkylene glycol glyceride, in which the glycol glyceride is a mixture of glyceryl and polyethylene glycol esters of one or more $C_8$-$C_{18}$ saturated fatty acids.

Two manufacture processes of such compositions are described hereafter.
Composition A:

Gelucire 44/14 (82 parts) is melted by heating to 60 DEG C. Powdered MIDOSTAURIN (18 parts) is added to the molten material. The resulting mixture is homogenised and the dispersion obtained is introduced into hard gelatin capsules of different size, so that some contain a 25 mg dosage and others a 75 mg dosage of the MIDOSTAURIN. The resulting capsules are suitable for oral administration.
Composition B:

Gelucire 44/14 (86 parts) is melted by heating to 60 DEG C. Powdered MIDOSTAURIN (14 parts) is added to the molten material. The mixture is homogenised and the dispersion obtained is introduced into hard gelatin capsules of different size, so that some contain a 25 mg dosage and others a 75 mg dosage of the MIDOSTAURIN. The resulting capsules are suitable for oral administration.

Gelucire 44/14 available commercially from Galtefosse; is a mixture of esters of $C_8$-$C_{18}$ saturated fatty acids with glycerol and a polyethylene glycol having a molecular weight of about 1500, the specifications for the composition of the fatty acid component being, by weight, 4-10% caprylic acid, 3-9% capric add, 40-50% lauric acid, 14-24% myristic acid, 4-14% palmitic acid and 5-15% stearic acid.

A preferred example of Gelucire formulation consists of:
Gelucire (44/14): 47 g
MIDOSTAURIN: 3.0 g filled into a 60 mL Twist off flask A Preferred example of soft gel will contain the following Microemulsion:

| | |
|---|---:|
| Cornoil glycerides | 85.0 mg |
| Polyethylenglykol 400 | 128.25 mg |
| Cremophor RH 40 | 213.75 mg |
| MIDOSTAURIN | 25.0 mg |
| DL alpha Tocopherol | 0.5 mg |
| Ethanol absolute | 33.9 mg |
| Total | 486.4 mg |

However, it should be clearly understood that it is for purposes of illustration only.

In a preferred embodiment this invention relates to use or method as described herein, wherein the daily effective amount of the compound of formula VII, is 100 to 300 mg, preferably 125 mg to 250 mg most preferably 220 to 230 mg, preferably 225 mg.

Most preferably the compound of formula VII, is administered once, two or three times a day, for a total dose of 100 to 300 mg daily.

In a very preferred embodiment the compound of formula VII, is administered three times a day, for a total dose of 220 to 230 preferably 225 mg daily, and preferably at a dose per administration of 70 to 80 mg, preferably 75 mg.

In still another embodiment, this invention relates to an article of manufacture comprising packaging material, and N-[(9S,10R,11R,13R)-2,3,10,11,12,13-hexahydro-10-methoxy-9-methyl-1-oxo-9,13-epoxy-1H,9H-diindolo[1,2,3-gh: 3',2',1'-Im]pyrrolo[3,4-j][1,7]benzodiazonin-11-yl]-N-methylbenzamide of the formula (VII) or a pharmaceutically acceptable salts thereof, contained within said packaging material, wherein said packaging material comprises label directions which indicate that said compound of formula (VII), or said pharmaceutically-acceptable salt, is to be administered to mammals suffering from diseases involving deregulated FLT3 receptor tyrosine kinase activity, in an amount from 50 to 500 mg, preferably 100 to 300 mg, preferably 125 mg to 250 mg, preferably 220 to 230 mg most preferably 225 mg following a specific dosage regimen to inhibit the development of diseases involving deregulated FLT3 receptor tyrosine kinase activity. Preferably to an article of manufacture wherein the compound of formula VII, is administered three times a day, for a total dose of 220 to 230 mg, preferably 225 mg daily, and preferably a dose of 70 to 80 mg most preferably 75 mg per administration for treating leukemias, especially acute myeloblastic leukemia and high risk myelodysplastic syndromes. A preferred embodiment relates to an article of manufacture comprising softgel capsules containing 25 mg of the compound of formula VII.

The efficacy of STAUROSPORINE DERIVATIVES for the treatment of diseases involving deregulated FLT3 receptor tyrosine kinase activity is illustrated by the results of the following pharmacological tests (examples 1 to 2). These examples illustrate the invention without in any way limiting its scope.

EXAMPLE 1

Flt-3 (Production and Measure of Activity)

The baculovirus donor vector pFbacG01 was used to generate a recombinant baculovirus that expresses the amino acid region amino acids 563-993 of the intra-cytoplasmic kinase domains of human Flt-3. The coding sequences for the cytoplasmic domain of Flt-3 was amplified by PCR from human c-DNA libraries (Clontech). The amplified DNA fragments and the pFbacG01 vector were made compatible for ligation by digestion with BamH1 and Hind III. Ligation of these DNA fragments resulted in the baculovirus donor plasmid Flt-3(1.1). The production of the viruses, the expression of proteins in Sf9 cells and the purification of the GST-fused proteins were performed as following:

(Generation of Bac-to Bac GST-fusion vectors); pFbacG01, pFbacGST2T and pFbacGSTx3 Bac-to-Bac™ donor vectors were generated from pAcG1, pAcG2T and pAcG3X respectively, which facilitate the expression of GST-fusion proteins with the possibility of cleavage with thrombin (pFbacGT2) or factor Xa (pFbacGSTx3) while pFbacG01 expresses no proteolytic cleavage site. These were generated in house by isolation of the DNA fragment containing the gene for GST with the C-terminal protease and restriction sites by restriction enzyme digestion of the relevant PharMingen baculovirus donor vector with EcoRV and EcoRI. This EcoRV/EcoRI fragment was ligated into the pFastBac1 vector which had been restriction digested with BamHI, blunt-ended by Klenow reaction and subsequently digested with EcoRI to generate a blunt-ended/EcoRI vector.

(Production of virus); Transfer vectors containing the kinase domains were transfected into the DH10Bac cell line (GIBCO) and plated on selective agar plates. Colonies without insertion of the fusion sequence into the viral genome (carried by the bacteria) are blue. Single white colonies were picked and viral DNA (bacmid) isolated from the bacteria by standard plasmid purification procedures. Sf9 cells or Sf21 cells were then transfected in 25 cm$^2$ flasks with the viral DNA using Cellfectin reagent.

(Determination of small scale protein expression in Sf9 cells); Virus containing media was collected from the transfected cell culture and used for infection to increase its titer. Virus containing media obtained after two rounds of infection was used for large-scale protein expression. For large-scale protein expression 100 cm$^2$ round tissue culture plates were seeded with 5×10$^7$ cells/plate and infected with 1 mL of virus-containing media (approx. 5 MOIs). After 3 days the cells were scraped off the plate and centrifuged at 500 rpm for 5 min. Cell pellets from 10-20, 100 cm$^2$ plates, were resuspended in 50 mL of ice-cold lysis buffer (25 mMTris-HCl, pH7.5, 2 mMEDTA, 1% NP-40, 1 mM DTT, 1 mMP MSF). The cells were stirred on ice for 15 min and then centrifuged at 5000 rpms for 20 min.

(Purification of GST-tagged proteins); The centrifuged cell lysate was loaded onto a 2 mL glutathione-sepharose column (Pharmacia) and washed three times with 10 mL of 25 mM Tris-HCl, pH 7.5, 2 mM EDTA, 1 mM DTT, 200 mM NaCl. The GST-tagged proteins were then eluted by 10 applications (1 mL each) of 25 mM Tris-HCl, pH 7.5, 10 mM reduced-glutathione, 100 mM NaCl, 1 mM DTT, 10% Glycerol and stored at −70° C.

Tyrosine protein kinase assays with purified GST-Flt-3 was carried in a final volume of 30 μL containing 200-1800 ng of enzyme protein (depending on the specific activity), 20 mM Tris-HCl, pH 7.6, 3 mM MnCl$_2$,3 mM MgCl$_2$, 1 mM DTT, 10 μM Na$_3$VO$_4$, 3 μg/mL poly(Glu,Tyr) 4:1, 1% DMSO, 8.0 μM ATP, [γ$^{33}$P] ATP 0.1 μCi). The activity was assayed in the presence or absence of inhibitors, by measuring the incorporation of $^{33}$P from [γ$^{33}$P] ATP into appropriate substrates. The assay (30 μL) was carried out in 96-well plates at ambient temperature for 20 min under conditions described below and terminated by the addition of 20 μL of 125 mM EDTA. Subsequently, 40 μL of the reaction mixture were transferred onto Immobilon-PVDF membrane (Millipore, Bedford, Mass., USA) previously soaked for 5 min with methanol, rinsed with water, then soaked for 5 min with 0.5% H$_3$PO$_4$ and mounted on vacuum manifold with disconnected vacuum source. After spotting all samples, vacuum was connected and each well rinsed with 200 μL 0.5% H$_3$PO$_4$. Membranes were removed and washed 4× on a shaker with 1.0% H$_3$PO$_4$, once with ethanol. Membranes were counted after drying at ambient temperature, mounting in Packard TopCount 96-well frame, and addition of 10 μL/well of Microscint™ (Packard). IC50 values were calculated by linear regression analysis of the percentage inhibition of each compound in duplicate, at four concentrations (usually 0.01, 0.1, 1 and 10 μM). One unit of protein kinase activity is defined as 1 nmole of $^{33}$P ATP transferred from [γ$^{33}$P] ATP to the substrate protein per minute per mg of protein at 37° C.

The activity was assayed in the presence or absence of inhibitors, by measuring the incorporation of $^{33}$P from [γ$^{33}$P] ATP into appropriate substrates. In this assay MIDOSTAURIN inhibits the transfer of the gamma phosphate of ATP onto OH of Tyrosines in the protein substrate by the Flt-3 kinase in the range of 0.1 to 1.0 μM.

EXAMPLE 2

Screening Assay for Inhibitors of FLT3

A cell based assay is utilised to identify inhibitors of mutant FLT3 tyrosine kinase receptors. The general technique involves comparing the effects of possible inhibitors on cell lines that depended on mutant FLT3 for proliferation, versus cell lines that do not depend on mutant FLT3 for proliferation. Compounds that have differential activity (more than or equal to 10 fold difference in sensitivity between FLT3+ cell lines and FLT3− cell lines) are selected for further study.

The cell lines used for the initial screening are sublines of Ba/F3 cells that are engineered to to express mutant or overexpress wild-type (non-mutated) FLT3 following infection with a retrovirus expressing appropriate FLT3 cDNAs. The parent cell line, Ba/F3 is dependent on interleukin-3 for proliferation, and when deprived of IL-3, the cells rapidly cease proliferation and die. The retrovirus expresses FLT3 from the retroviral LTR and the neo gene from an IRES site. Ba/F3 cells were selected in G418 and analyzed for expression of FLT3 by fluorescence activated cell sorting (FACS). Cell lines with two different FLT3 mutations are used. One mutant expresses a FLt-3 that has a 14 amino acid duplication in the juxtamembrane domain encoded by exon 11, the specific duplication being . . . VDFREYEYDLKWEF . . . (termed, Ba/F3-FLT3-ITD) The second mutation has a point mutation that converts asparagines at position 835 to tyrosine (termed Ba/F3-FLT3-D835Y). Both mutations increase the Flt-3 kinase activity and makes it independent of IL-3. Ba/F3 cells expressing wild type FLT3 are similarly generated and used as the "control" cell line. The parental (uninfected) cell line, and the wild-type "control" cell line remain dependent on interleukin-3 for proliferation. The cells expressing either of the mutants become independent of interleukin-3 for proliferation. These cell lines were obtained from Gary Gilliland, M.D., Brigham and Womens' Hospital, Boston, Mass. An additional Ba/F3 cell line expressing a different tandem duplication mutant of FLT3 has been generated using similar techniques.

Ba/F3 cells (-control, -FLT3-ITD, or -FLT3-D835Y) are cultured at 50,000 cells/mL in 2 mL cultures, with RPMI 1640 with 10% fetal calf serum as the culture medium. The medium for the control cells, but not the mutant-FLT3 cells) contains 10% (VN) conditioned medium from the WEHI-3B cell line as a source of interleukin-3. A 10 mM "stock" solution of each compound is made in dimethylsufoxide (DMSO). Dilutions sre then made into RPMI 1640 with 10% fetal calf serum to create final drug concentrations ranging from typically one nanomolar to 10 micromolar. Similar dilutions are made of DMSO to serve as vehicle controls. At 24, 48, and 72 hours after addition of compounds, aliquots of cells are removed and counted manually on a hemocytometer chamber after staining with 1% trypan blue in phosphate buffered saline.

Compounds that are selectively more toxic to Ba/F3-FLT3-ITD cells than to wild type control Ba/F3 cells are further studied against the additional FLT3-mutant expressing cells. Also, antibodies to FLT3 are used to immunoprecipitate FLT3 proteins before, and after, exposure to various concentrations of active compounds. The immunoprecipitated proteins are separated by sodium dodecyl sulfate polyacrylamide gels, transferred electrophoretically to paper, and immunoblotted with an antibody to phosphotyrosine. This assay determines if compounds reduced the "autophosphorylation" of FLT3 that is characteristic of the mutated forms of the receptor.

MIDOSTAURIN, inhibited proliferation of both Ba/F3-FLT3-ITD and Ba/F3-D835Y cells at an IC50 of <10 nM, and induced both G1 cell cycle arrest and apoptosis in 24-72 hours. MIDOSTAURIN did not inhibit growth of untransformed Ba/F3 cells at concentrations of up to 500 nM, and the growth inhibitory effects of MIDOSTAURIN on Ba/F3-FLT3-ITD cells could be reversed by the addition of high concentrations of IL-3 to provide an alternative viability signal. At the concentrations required to inhibit the proliferation of FLT3-dependent cell-lines, MIDOSTAURIN was not cytotoxic against several human leukemia and lymphoma cell lines that did not have mutant FLT3 receptors, suggesting that the drug has an unexpected high degree of specificity as a cytoxic agent. Overall, these results indicate that MIDOSTAURIN is a potent inhibitor of mutant FLT3 receptor tyrosine kinase activity and is a promising candidate for testing as an anti-leukemia agent in patients with mutant FLT3 receptors.

Biological data obtained as percent inhibition of Flt3 kinase activity at a 1.0 micromolar concentration is given for the compounds mentioned in the below table I.

TABLE I

| Chem. Abstr. Registry Number | Flt3 Inhibition | Name |
|---|---|---|
| 62996-74-1 | 100% | (9S,10R,11R,13R)-2,3,10,11,12,13-Hexahydro-10-methoxy-9-methyl-11-(methylamino)-9,13-epoxy-1H, 9H-diindolo[1,2,3-gh:3',2',1'-lm]pyrrolo[3,4-j][1,7]benzodiazonin-1-one, |
| 120685-21-4 | 82% | [9S-(9a,10b,11b,13a)]-N-(2,3,10,11,12,13-Hexahydro-10-methoxy-9-methyl-1-oxo-9,13-epoxy-1H,9H-diindolo[1,2,3-gh:3',2',1'-lm]pyrrolo[3,4-j][1,7]benzodiazonin-11-yl)-N-methyl-glycine, methyl ester, |
| 120685-22-5 | 98% | [9S-(9a,10b,11b,13a)]-N-(2,3,10,11,12,13-Hexahydro-10-methoxy-9-methyl-1-oxo-9,13-epoxy-1H,9H-diindolo[1,2,3-gh:3',2',1'-lm]pyrrolo[3,4-j][1,7]benzodiazonin-11-yl)-N-methyl-glycine, |
| 120685-26-9 | 97% | [9S-(9a,10b,11b,13a)]-2,3,10,11,12,13-Hexahydro-10-methoxy-N,N,N,9-tetramethyl-1-oxo-9,13-epoxy-1H,9H-diindolo [1,2,3-gh:3',2',1'-lm]pyrrolo[3,4-j][1,7]benzodiazonin-11-aminium iodide |
| 120685-12-3 | 66% | 2,2,2-Trifluoro-N-[(9S,10R,11R,13R)-2,3,10,11,12,13-hexahydro-10-methoxy-9-methyl-1-oxo-9,13-epoxy-1H,9H-diindolo [1,2,3-gh:3',2',1'-lm]pyrrolo[3,4-j][1,7]benzodiazonin-11-yl]-N-methyl-acetamide, |
| 120685-13-4 | 91% | (9a,10b,11b,13a)-N-(2,3,10,11,12,13-Hexahydro-10-methoxy-9-methyl-1-oxo-9,13-epoxy-1H,9H-diindolo[1,2,3-gh:3',2',1'-lm]pyrrolo [3,4-j][1,7]benzodiazonin-11-yl)-N,N'-dimethyl-thiourea |
| 120685-39-4 | 93% | (9a,10b,11b,13a)-N-(2,3,10,11,12,13-Hexahydro-10-methoxy-9-methyl-1-oxo-9,13-epoxy-1H,9H-diindolo [1,2,3-gh:3',2',1'-lm]pyrrolo[3,4-j][1,7]benzodiazonin-11-yl)-N-methyl-N'-2-propenyl-thiourea |
| 120685-10-1 | 98% | [9S-(9a,10b,11b,13a)]-4-[(2,3,10,11,12,13-Hexahydro-10-methoxy-9-methyl-1-oxo-9,13-epoxy-1H,9H-diindolo [1,2,3-gh:3',2',1'-lm]pyrrolo[3,4-j][1,7]benzodiazonin-11-yl)methylamino]-4-oxo-butanoic acid, sodium salt, |
| 120685-28-1 | 100% | N-Ethyl-[9S-(9a,10b,11b,13a)]-2,3,10,11,12,13-hexahydro-10-methoxy-N,N,9-trimethyl-1-oxo-9,13-epoxy-1H,9H-diindolo [1,2,3-gh:3',2',1'-lm]pyrrolo[3,4-j][1,7]benzodiazonin-11-aminium iodide, |

TABLE I-continued

| Chem. Abstr. Registry Number | Flt3 Inhibition | Name |
|---|---|---|
| 120685-17-8 | 33% | [9S-(9a,10b,11b,13a)]-(2,3,10,11,12,13-Hexahydro-10-methoxy-9-methyl-1-oxo-9,13-epoxy-1H,9H-diindolo [1,2,3-gh:3',2',1'-lm]pyrrolo[3,4-j][1,7]benzodiazonin-11-yl)methyl-carbamic acid, 1,1-dimethylethyl ester |
| 120685-15-6 | 74% | (9a,10b,11b,13a)-N-(2,3,10,11,12,13-Hexahydro-10-methoxy-9-methyl-1-oxo-9,13-epoxy-1H,9H-diindolo [1,2,3-gh:3',2',1'-lm]pyrrolo[3,4-j][1,7]benzodiazonin-11-yl)-N-methyl-3-nitro-benzamide |
| 120685-44-1 | 55% | (9a,10b,11b,13a)-4-Fluoro-N-(2,3,10,11,12,13-hexahydro-10-methoxy-9-methyl-1-oxo-9,13-epoxy-1H,9H-diindolo [1,2,3-gh:3',2',1'-lm]pyrrolo[3,4-j][1,7]benzodiazonin-11-yl)-N-methyl-benzamide |
| 157318-74-6 | | [9S-(9a,10b,11b,13a)]-4-[[(2,3,10,11,12,13-Hexahydro-10-methoxy-9-methyl-1-oxo-9,13-epoxy-1H,9H-diindolo [1,2,3-gh:3',2',1'-lm]pyrrolo[3,4-j][1,7]benzodiazonin-11-yl)methylamino]carbonyl]-benzoic acid |
| 120751-44-2 | 90% | [9S-(9a,10b,11b,13a)]-4-[[(2,3,10,11,12,13-Hexahydro-10-methoxy-9-methyl-1-oxo-9,13-epoxy-1H,9H-diindolo [1,2,3-gh:3',2',1'-lm]pyrrolo[3,4-j][1,7]benzodiazonin-11-yl)methylamino]carbonyl]-benzoic acid, monosodium salt |
| 120685-16-7 | 60% | (9a,10b,11b,13a)-3-Fluoro-N-(2,3,10,11,12,13-hexahydro-10-methoxy-9-methyl-1-oxo-9,13-epoxy-1H,9H-diindolo [1,2,3-gh:3',2',1'-lm]pyrrolo[3,4-j][1,7]benzodiazonin-11-yl)-N-methyl-benzamide |
| 120685-46-3 | 81% | (9a,10b,11b,13a)-N-(2,3,10,11,12,13-Hexahydro-10-methoxy-9-methyl-1-oxo-9,13-epoxy-1H,9H-diindolo [1,2,3-gh:3',2',1'-lm]pyrrolo[3,4-j][1,7]benzodiazonin-11-yl)-N-methyl-4-nitro-benzamide |
| 120685-18-9 | 63% | [9S-(9a,10b,11b,13a)]-N-(2,3,10,11,12,13-Hexahydro-10-methoxy-9-methyl-1-oxo-9,13-epoxy-1H,9H-diindolo [1,2,3-gh:3',2',1'-lm]pyrrolo[3,4-j][1,7]benzodiazonin-11-yl)-N-methyl-3,5-dinitro-benzamide |
| 124078-43-9 | 65% | [9S-(9a,10b,11b,13a)]-[2-[(2,3,10,11,12,13-Hexahydro-10-methoxy-9-methyl-1-oxo-9,13-epoxy-1H,9H-diindolo [1,2,3-gh:3',2',1'-lm]pyrrolo[3,4-j][1,7]benzodiazonin-11-yl)methylamino]-2-oxoethyl]-carbamic acid, 1,1-dimethylethyl ester |
| 124151-42-4 | 97% | [9S-(9a,10b,11b,13a)]-2-Amino-N-(2,3,10,11,12,13-hexahydro-10-methoxy-9-methyl-1-oxo-9,13-epoxy-1H,9H-diindolo [1,2,3-gh:3',2',1'-lm]pyrrolo[3,4-j][1,7]benzodiazonin-11-yl)-N-methyl-acetamide, monohydrochloride, |
| 125035-78-1 | 52% | (9a,10b,11b,13a)-[2-[(2,3,10,11,12,13-Hexahydro-10-methoxy-9-methyl-1-oxo-9,13-epoxy-1H,9H-diindolo [1,2,3-gh:3',2',1'-lm]pyrrolo[3,4-j][1,7]benzodiazonin-11-yl)methylamino]-2-oxoethyl]-carbamic acid, phenylmethyl ester |
| 154590-03-1 | 49% | [9S-(9a,10b,11b,13a)]-(2,3,10,11,12,13-Hexahydro-10-methoxy-9-methyl-1-oxo-9,13-epoxy-1H,9H-diindolo [1,2,3-gh:3',2',1'-lm]pyrrolo[3,4-j][1,7]benzodiazonin-11-yl)methyl-carbamic acid, 2-methylpropyl ester |
| 154589-96-5 | 63% | [9S-(9a,10b,11b,13a)]-N-(2,3,10,11,12,13-Hexahydro-10-methoxy-9-methyl-1,3-dioxo-9,13-epoxy-1H,9H-diindolo [1,2,3-gh:3',2',1'-lm]pyrrolo[3,4-j][1,7]benzodiazonin-11-yl)-N-methyl-benzamide |
| 174291-07-7 | | [9R-(9a,10b,11b,13a)]-10,11,12,13-Tetrahydro-10-methoxy-9-methyl-11-(methylamino)-9,13-epoxy-1H,9H-diindolo [1,2,3-gh:3',2',1'-lm]pyrrolo[3,4-j][1,7]benzodiazonine-1,3(2H)-dione, |
| 154589-93-2 | 67% | [9S-(9a,10b,11b,13a)]-(2,3,10,11,12,13-Hexahydro-10-methoxy-9-methyl-1,3-dioxo-9,13-epoxy-1H,9H-diindolo [1,2,3-gh:3',2',1'-lm]pyrrolo[3,4-j][1,7]benzodiazonin-11-yl)methyl-carbamic acid, 1,1-dimethylethyl ester, |
| 112953-11-4 | | (3R,9S,10R,11R,13R)-2,3,10,11,12,13-Hexahydro-3-hydroxy-10-methoxy-9-methyl-11-(methylamino)-9,13-epoxy-1H,9H-diindolo [1,2,3-gh:3',2',1'-lm]pyrrolo[3,4-j][1,7]benzodiazonin-1-one |
| 126221-76-9 | 83% | (9S,10R,11Z,13R)-2,3,9,10,12,13-Hexahydro-10-methoxy-9-methyl-9,13-epoxy-1H,11H-diindolo [1,2,3-gh:3',2',1'-lm]pyrrolo[3,4-j][1,7]benzodiazonine-1,11-dione, 11-oxime |
| 149622-43-5 | 66% | 11-[[N-Acetyl-1-O-methyl-4,6-O-(phenylmethylene)-a-normuramoyl]methylamino]-2,3,10,11,12,13-hexahydro-10-methoxy-9-methyl-9,13-epoxy-1H,9H-diindolo[1,2,3-gh:3',2',1'-lm]pyrrolo[3,4-j][1,7]benzodiazonin-1-one |
| 178276-05-6 | | (9S,10S,13R)-2,3,9,10,12,13-Hexahydro-10-methoxy-9-methyl-9,13-epoxy-1H,11H-diindolo[1,2,3-gh:3',2',1'-lm]pyrrolo[3,4-j][1,7]benzodiazonine-1,11-dione |
| 178276-05-6 | 88% | (9S,10S,13R)-2,3,9,10,12,13-Hexahydro-10-methoxy-9-methyl-9,13-Epoxy-1H,11H-diindolo[1,2,3-gh:3',2',1'-lm]pyrrolo [3,4-j][1,7]benzodiazonine-1,11-dione |

TABLE I-continued

| Chem. Abstr. Registry Number | Flt3 Inhibition | Name |
|---|---|---|
| 149622-59-3 | 77% | (9a,10b,11b,13a)-11-[[N-Acetyl-4,6-O-(1-methylethylidene)-1-O-(phenylmethyl)-a-isomuramoyl]methylamino]-2,3,10,11,12,13-hexahydro-9-methyl-10-methoxy-9,13-epoxy-1H,9H-diindolo[1,2,3-gh:3',2',1'-lm]pyrrolo[3,4-j][1,7]benzodiazonin-1-one |
| 178955-60-7 | 89% | N-[(9S,10R,11R,13R)-2,3,10,11,12,13-Hexahydro-10-methoxy-9-methyl-1-oxo-9,13-epoxy-1H,9H-diindolo[1,2,3-gh:3',2',1'-lm]pyrrolo[3,4-j][1,7]benzodiazonin-11-yl]-2-hydroxy-N-methyl-Benzamide |
| 165815-73-6 | 91% | N-[(9S,10R,11R,13R)-2,3,10,11,12,13-Hexahydro-10-methoxy-9-methyl-1-oxo-9,13-epoxy-1H,9H-diindolo[1,2,3-gh:3',2',1'-lm]pyrrolo[3,4-j][1,7]benzodiazonin-11-yl]-4-hydroxy-N-methyl-benzamide, |
| 149622-39-9 | 72% | (9a,10b,11b,13a)-11-[[N-Acetyl-1-O-(phenylmethyl)-a-muramoyl]methylamino]-2,3,10,11,12,13-hexahydro-10-methoxy-9-methyl-9,13-epoxy-1H,9H-diindolo[1,2,3-gh:3',2',1'-lm]pyrrolo[3,4-j][1,7]benzodiazonin-1-one |
| 129623-30-9 | | (9S,10R,11R,13R)-11-(Dimethylamino)-2,3,10,11,12,13-hexahydro-10-methoxy-9-methyl-9,13-epoxy-1H,9H-diindolo[1,2,3-gh:3',2',1'-lm]pyrrolo[3,4-j][1,7]benzodiazonin-1-one, |
| 112953-11-4 | | (3R,9S,10R,11R,13R)-2,3,10,11,12,13-Hexahydro-3-hydroxy-10-methoxy-9-methyl-11-(methylamino)-9,13-epoxy-1H,9H-diindolo[1,2,3-gh:3',2',1'-lm]pyrrolo[3,4-j][1,7]benzodiazonin-1-one |
| 155848-16-1 | 89% | [9S-(9a,10b,11b,13a)]-N-(2,3,10,11,12,13-Hexahydro-10-methoxy-9-methyl-1-oxo-9,13-epoxy-1H,9H-diindolo[1,2,3-gh:3',2',1'-lm]pyrrolo[3,4-g][1,7]benzodiazonin-11-yl)-N-methyl-3-pyridinecarboxamide |
| 155848-17-2 | 85% | [9S-(9a,10b,11b,13a)]-N-(2,3,10,11,12,13-Hexahydro-10-methoxy-9-methyl-1-oxo-9,13-epoxy-1H,9H-diindolo[1,2,3-gh:3',2',1'-lm]pyrrolo[3,4-g][1,7]benzodiazonin-11-yl)-N-methyl-pyrazinecarboxamide |
| 178276-00-1 | | 2,3,9,10,12,13-Hexahydro-3-hydroxy-10-methoxy-9-methyl-9,13-epoxy-1H,11H-diindolo[1,2,3-gh:3',2',1'-lm]pyrrolo[3,4-j][1,7]benzodiazonine-1,11-dione, 11-oxime |
| 161927-20-4 | | [9S-(9a,10b,11a,13a)]-N-(2,3,10,11,12,13-Hexahydro-10-methoxy-9-methyl-1-oxo-9,13-epoxy-1H,9H-diindolo[1,2,3-gh:3',2',1'-lm]pyrrolo[3,4-j][1,7]benzodiazonin-11-yl)-N-hydroxy-formamide, |
| 179237-49-1 | 41% | N-(2,3,10,11,12,13-Hexahydro-3-hydroxy-10-methoxy-9-methyl-1-oxo-9,13-epoxy-1H,9H-diindolo[1,2,3-gh:3',2',1'-lm]pyrrolo[3,4-j][1,7]benzodiazonin-11-yl)-N-methyl-benzamide |
| 155848-20-7 | | [3R-(3a,9b,10a,11a,13b)]-N-(2,3,10,11,12,13-Hexahydro-3-hydroxy-10-methoxy-9-methyl-1-oxo-9,13-epoxy-1H,9H-diindolo[1,2,3-gh:3',2',1'-lm]pyrrolo[3,4-j][1,7]benzodiazonin-11-yl)-N-methyl-benzamide |
| 149622-41-3 | 51% | (9a,10b,11b,13a)-11-[[N-Acetyl-6-O-(methylsulfonyl)-1-O-(phenylmethyl)-a-muramoyl]methylamino]-2,3,10,11,12,13-hexahydro-10-methoxy-9-methyl-, 9,13-epoxy-1H,9H-diindolo[1,2,3-gh:3',2',1'-lm]pyrrolo[3,4-j][1,7]benzodiazonin-1-one |
| 149713-64-4 | 76% | (9a,10b,11b,13a)-11-[[N-Acetyl-1-O-(phenylmethyl)-a-isomuramoyl]methylamino]-2,3,10,11,12,13-hexahydro-10-methoxy-9-methyl-9,13-epoxy-1H,9H-diindolo[1,2,3-gh:3',2',1'-lm]pyrrolo[3,4-j][1,7]benzodiazonin-1-one, |
| 149622-54-8 | 94% | (9a,10b,11b,13a)-11-[[N-Acetyl-6-O-(methylsulfonyl)-a-muramoyl]methylamino]-2,3,10,11,12,13-hexahydro-10-methoxy-9-methyl-9,13-epoxy-1H,9H-diindolo[1,2,3-gh:3',2',1'-lm]pyrrolo[3,4-j][1,7]benzodiazonin-1-one, |
| 149622-53-7 | 91% | (9a,10b,11b,13a)-11-[(N-Acetyl-a-muramoyl)methylamino]-2,3,10,11,12,13-hexahydro-10-methoxy-9-methyl-9,13-epoxy-1H,9H-diindolo[1,2,3-gh:3',2',1'-lm]pyrrolo[3,4-j][1,7]benzodiazonin-1-one |
| 149622-42-4 | 61% | (9a,10b,11b,13a)-11-[[N-Acetyl-6-azido-6-deoxy-1-O-(phenylmethyl)-a-muramoyl]methylamino]-2,3,10,11,12,13-hexahydro-10-methoxy-9-methyl-,9,13-epoxy-1H,9H-diindolo[1,2,3-gh:3',2',1'-lm]pyrrolo[3,4-j][1,7]benzodiazonin-1-one, |
| 150622-14-3 | 99% | (9a,10b,11b,13a)-11-[[N-Acetyl-6-amino-6-deoxy-1-O-(phenylmethyl)-a-muramoyl]methylamino]-2,3,10,11,12,13-hexahydro-10-methoxy-9-methyl-9,13-epoxy-1H,9H-diindolo[1,2,3-gh:3',2',1'-lm]pyrrolo[3,4-j][1,7]benzodiazonin-1-one, monomethanesulfonate |
| 149622-56-0 | 100% | (9a,10b,11b,13a)-11-[(N-Acetyl-6-amino-6-deoxy-a-isomuramoyl)methylamino]-2,3,10,11,12,13-hexahydro-10-methoxy-9-methyl-9,13-epoxy-1H,9H-diindolo[1,2,3-gh:3',2',1'-lm]pyrrolo[3,4-j][1,7]benzodiazonin-1-one, , |
| 149713-77-9 | 96% | (9a,10b,11b,13a)-11-[(N-Acetyl-6-amino-6-deoxy-b-muramoyl)methylamino]-2,3,10,11,12,13-hexahydro-10-methoxy-9-methyl-9,13-epoxy-1H,9H-diindolo[1,2,3-gh:3',2',1'-lm]pyrrolo[3,4-j][1,7]benzodiazonin-1-one |

TABLE I-continued

| Chem. Abstr. Registry Number | Flt3 Inhibition | Name |
|---|---|---|
| 149622-55-9 | 85% | (9a,10b,11b,13a)-11-[(N-Acetyl-a-normuramoyl)methylamino]-2,3,10,11,12,13-hexahydro-10-methoxy-9-methyl-9,13-epoxy-1H,9H-diindolo[1,2,3-gh:3',2',1'-lm]pyrrolo[3,4-j][1,7]benzodiazonin-1-one |
| 149622-45-7 | 43% | [9a,10b,11b(S*),13a]-phenylmethyl 2-(acetylamino)-2-deoxy-3-O-[1-[[(2,3,10,11,12,13-hexahydro-10-methoxy-9-methyl-1-oxo-9,13-epoxy-1H,9H-diindolo[1,2,3-gh:3',2',1'-lm]pyrrolo[3,4-j][1,7]benzodiazonin-11-yl)methylamino]carbonyl]propyl]-a-D-Glucopyranoside |
| 149622-60-6 | 76% | [9a,10b,11b(S*),13a]-2-(Acetylamino)-2-deoxy-3-O-[1-[[(2,3,10,11,12,13-hexahydro-10-methoxy-9-methyl-1-oxo-9,13-epoxy-1H,9H-diindolo[1,2,3-gh:3',2',1'-lm]pyrrolo[3,4-j][1,7]benzodiazonin-11-yl)methylamino]carbonyl]propyl]-a-D-Glucopyranose |
| 149622-61-7 | 70% | (9a,10b,11b,13a)-11-[[N-Acetyl-4,6-di-O-acetyl-1-O-(phenylmethyl)-a-muramoyl]methylamino]-2,3,10,11,12,13-hexahydro-10-methoxy-9-methyl-9,13-epoxy-1H,9H-diindolo[1,2,3-gh:3',2',1'-lm]pyrrolo[3,4-j][1,7]benzodiazonin-1-one, |
| 149622-62-8 | 22% | (9a,10b,11b,13a)-11-[[N-Acetyl-4-O-acetyl-6-O-(1-oxooctadecyl)-1-O-(phenylmethyl)-a-muramoyl]methylamino]-2,3,10,11,12,13-hexahydro-10-methoxy-9-methyl-9,13-epoxy-1H,9H-diindolo[1,2,3-gh:3',2',1'-lm]pyrrolo[3,4-j][1,7]benzodiazonin-1-one |
| 160335-31-9 | 90% | [9S-[9a,10b,11b(R*),13a]]-N-(2,3,10,11,12,13-Hexahydro-10-methoxy-9-methyl-1-oxo-9,13-epoxy-1H,9H-diindolo[1,2,3-gh:3',2',1'-lm]pyrrolo[3,4-j][1,7]benzodiazonin-11-yl)-N-methyl-2-[(tetrahydro-2H-pyran-4-yl)oxy]-propanamide |
| 149622-49-1 | 74% | 11-[[N-Acetyl-1-deoxy-4,6-O-(phenylmethylene)muramoyl]methylamino]-2,3,10,11,12,13-hexahydro-10-methoxy-9-methyl-9,13-epoxy-1H,9H-diindolo[1,2,3-gh:3',2',1'-lm]pyrrolo[3,4-j][1,7]benzodiazonin-1-one |
| 149622-63-9 | 98% | (9a,10b,11b,13a)-11-[(N-Acetyl-1-deoxymuramoyl)methylamino]-2,3,10,11,12,13-hexahydro-10-methoxy-9-methyl-9,13-epoxy-1H,9H-diindolo[1,2,3-gh:3',2',1'-lm]pyrrolo[3,4-j][1,7]benzodiazonin-1-one |
| 149622-64-0 | 27% | (9a,10b,11b,13a)-11-[[N-Acetyl-4-O-acetyl-6-O-(1-oxooctadecyl)-a-muramoyl]methylamino]-2,3,10,11,12,13-hexahydro-10-methoxy-9-methyl-9,13-epoxy-1H,9H-diindolo[1,2,3-gh:3',2',1'-lm]pyrrolo[3,4-j][1,7]benzodiazonin-1-one |
| 149622-65-1 | 74% | (9a,10b,11b,13a)-11-[[N-Acetyl-4,6-di-O-acetyl-a-muramoyl]methylamino]-2,3,10,11,12,13-hexahydro-10-methoxy-9-methyl-9,13-epoxy-1H,9H-diindolo[1,2,3-gh:3',2',1'-lm]pyrrolo[3,4-j][1,7]benzodiazonin-1-one, |
| 149622-66-2 | | (9a,10b,11b,13a)-11-[[N-Acetyl-1,4-di-O-acetyl-6-O-(1-oxooctadecyl)-a-muramoyl]methylamino]-2,3,10,11,12,13-hexahydro-10-methoxy-9-methyl-9,13-epoxy-1H,9H-diindolo[1,2,3-gh:3',2',1'-lm]pyrrolo[3,4-j][1,7]benzodiazonin-1-one |
| 126572-73-4 | | (9S,10R,11R,13R)-2,3,10,11,12,13-Hexahydro-11-hydroxy-10-methoxy-9-methyl-9,13-epoxy-1H,9H-diindolo[1,2,3-gh:3',2',1'-lm]pyrrolo[3,4-j][1,7]benzodiazonin-1-one |
| 187457-76-7 | | [9S-(9a,10b,13a)]-[[(2,3,9,10,12,13-Hexahydro-10-methoxy-9-methyl-1-oxo-9,13-epoxy-1H,11H-diindolo[1,2,3-gh:3',2',1'-lm]pyrrolo[3,4-j][1,7]benzodiazonin-11-ylidene)amino]oxy]-acetic acid |
| 149622-68-4 | 93% | (9a,10b,11b,13a)-11-[(N-Acetyl-6-O-acetyl-1-deoxymuramoyl)methylamino]-2,3,10,11,12,13-hexahydro-10-methoxy-9-methyl-,11-[(N-acetyl-6-O-acetyl-1-deoxymuramoyl)methylamino]-2,3,10,11,12,13-hexahydro-10-methoxy-9-methyl-9,13-epoxy-1H,9H-diindolo[1,2,3-gh:3',2',1'-lm]pyrrolo[3,4-j][1,7]benzodiazonin-1-one |
| 149622-70-8 | 67% | (9a,10b,11b,13a)-11-[[N-Acetyl-1-deoxy-6-O-[(4-methylphenyl)sulfonyl]muramoyl]methylamino]-2,3,10,11,12,13-hexahydro-10-methoxy-9-methyl-,9,13-epoxy-1H,9H-diindolo[1,2,3-gh:3',2',1'-lm]pyrrolo[3,4-j][1,7]benzodiazonin-1-one |
| 150654-80-1 | 97% | (9a,10b,11b,13a)-11-[(N-Acetyl-6-amino-1,6-dideoxymuramoyl)methylamino]-2,3,10,11,12,13-hexahydro-10-methoxy-9-methyl-9,13-epoxy-1H,9H-diindolo[1,2,3-gh:3',2',1'-lm]pyrrolo[3,4-j][1,7]benzodiazonin-1-one, monomethanesulfonate |
| 239785-03-6 | 100% | (9R,10S,11S,13S)-2,3,10,11,12,13-Hexahydro-10-hydroxy-9-methyl-11-(methylamino)-,9,13-epoxy-1H,9H-diindolo[1,2,3-gh:3',2',1'-lm]pyrrolo[3,4-j][1,7]benzodiazonin-1-one |
| 187457-78-9 | 77% | [9S-(9a,10b,13a)]-2,3,9,10,12,13-Hexahydro-10-methoxy-9-methyl-9,13-epoxy-1H,11H-diindolo[1,2,3-gh:3',2',1'-lm]pyrrolo[3,4-j][1,7]benzodiazonine-1,11-dione, 11-(O-acetyloxime) |
| 126221-77-0 | 96% | (9S,10R,11R,13R)-11-Amino-2,3,10,11,12,13-hexahydro-10-methoxy-9-methyl-9,13-epoxy-1H,9H-diindolo[1,2,3-gh:3',2',1'-lm]pyrrolo[3,4-j][1,7]benzodiazonin-1-one, |
| 160251-50-3 | 89% | [9S-[9a,10b,11b(S*),13a]]-N-(2,3,10,11,12,13-Hexahydro-10-methoxy-9-methyl-1-oxo-9,13-epoxy-1H,9H-diindolo[1,2,3-gh:3',2',1'-lm]pyrrolo[3,4-j][1,7]benzodiazonin-11-yl)-N-methyl-2-[(tetrahydro-2H-pyran-4-yl)oxy]-propanamide |

TABLE I-continued

| Chem. Abstr. Registry Number | Flt3 Inhibition | Name |
| --- | --- | --- |
| 160251-52-5 | 94% | [9S-(9a,10b,11b,13a)]-N-(2,3,10,11,12,13-Hexahydro-10-methoxy-9-methyl-1-oxo-9,13-epoxy-1H,9H-diindolo[1,2,3-gh:3',2',1'-lm]pyrrolo[3,4-j][1,7]benzodiazonin-11-yl)-N-methyl-2-[(tetrahydro-2H-pyran-4-yl)oxy]-acetamide |
| 187457-79-0 | | [9S-(9a,10b,13a)]-2,3,9,10,12,13-Hexahydro-10-methoxy-9-methyl-11-[(O-methylsulfonyl)oxime], 9,13-epoxy-1H,11H-diindolo[1,2,3-gh:3',2',1'-lm]pyrrolo[3,4-j][1,7]benzodiazonine-1,11-dione, |
| 149109-23-9 | | (9S,10R,11R,13R)-11-(Dimethyloxidoamino)-2,3,10,11,12,13-hexahydro-10-methoxy-9-methyl-9,13-epoxy-1H,9H-diindolo[1,2,3-gh:3',2',1'-lm]pyrrolo[3,4-j][1,7]benzodiazonin-1-one, |
| 160251-55-8 | 85% | [9S-(9a,10b,11b,13a)]-N-(2,3,10,11,12,13-Hexahydro-10-methoxy-9-methyl-1-oxo-9,13-epoxy-1H,9H-diindolo[1,2,3-gh:3',2',1'-lm]pyrrolo[3,4-j][1,7]benzodiazonin-11-yl)-N,2-dimethyl-2-[(tetrahydro-2H-pyran-4-yl)oxy]-propanamide |
| 187457-73-4 | 89% | [9S-(9a,10b,13a)]-2,3,9,10,12,13-Hexahydro-10-hydroxy-9-methyl-9,13-epoxy-1H,11H-diindolo[1,2,3-gh:3',2',1'-lm]pyrrolo[3,4-j][1,7]benzodiazonine-1,11-dione, 11-oxime, |
| 187457-73-4 | | as above |
| 406703-32-0 | | (9S,10R,11R,13R)-11-Amino-2,3,10,11,12,13-hexahydro-10-hydroxy-9-methyl-9,13-epoxy-1H,9H-diindolo[1,2,3-gh:3',2',1'-lm]pyrrolo[3,4-j][1,7]benodiazonin-1-one |
| 120685-11-2 | | N-[(9S,10R,11R,13R)-2,3,10,11,12,13-hexahydro-10-methoxy-9-methyl-1-oxo-9,13-epoxy-1H,9H-diindolo[1,2,3-gh:3',2',1'-lm]pyrrolo[3,4-j][1,7]benzodiazonin-11-yl]-N-methyl-benzamide |
| 187457-71-2 | | [9S-(9a,10b,11E,13a)]-2,3,9,10,12,13-Hexahydro-10-methoxy-9-methyl-,9,13-epoxy-1H,11H-diindolo[1,2,3-gh:3',2',1'-lm]pyrrolo[3,4-j][1,7]benzodiazonine-1,11-dione, 11-[O-(phenylmethyl)oxime], |
| 187457-75-6 | | [9S-(9a,10b,13a)]-2,3,9,10,12,13-Hexahydro-10-hydroxy-9-methyl-9,13-epoxy-1H,11H-diindolo[1,2,3-gh:3',2',1'-lm]pyrrolo[3,4-j][1,7]benzodiazonine-1,11-dione |
| 120685-37-2 | | (9a,10b,11b,13a)-(2,3,10,11,12,13-Hexahydro-10-methoxy-9-methyl-1-oxo-9,13-epoxy-1H,9H-diindolo[1,2,3-gh:3',2',1'-lm]pyrrolo[3,4-j][1,7]benzodiazonin-11-yl)methyl-carbamic acid, phenyl ester, |
| 120685-47-4 | | (9a,10b,11b,13a)-4-[[(2,3,10,11,12,13-Hexahydro-10-methoxy-9-methyl-1-oxo-9,13-epoxy-1H,9H-diindolo[1,2,3-gh:3',2',1'-lm]pyrrolo[3,4-j][1,7]benzodiazonin-11-yl)methylamino]carbonyl]-benzoic acid, methyl ester |
| 157318-74-6 | | [9S-(9a,10b,11b,13a)]-4-[[[(2,3,10,11,12,13-Hexahydro-10-methoxy-9-methyl-1-oxo-9,13-epoxy-1H,9H-diindolo[1,2,3-gh:3',2',1'-lm]pyrrolo[3,4-j][1,7]benzodiazonin-11-yl)methylamino]carbonyl]-benzoic acid |
| 159404-67-8 | 64% | (2,3,10,11,12,13-hexahydro-10-methoxy-9-methyl-1-oxo-9,13-epoxy-1H,9H-diindolo[1,2,3-gh:3',2',1'-lm]pyrrolo[3,4-j][1,7]benzodiazonin-11-yl)methyl-carbamic acid, phenylmethyl ester |
| 124078-41-7 | 99% | [9S-(9a,10b,11b,13a)]-3-Amino-N-(2,3,10,11,12,13-hexahydro-10-methoxy-9-methyl-1-oxo-9,13-epoxy-1H,9H-diindolo[1,2,3-gh:3',2',1'-lm]pyrrolo[3,4-j][1,7]benzodiazonin-11-yl)-N-methyl-propanamide, monohydrochloride, |
| 124078-44-0 | 87% | [9S-(9a,10b,11b,13a)]-[3-[(2,3,10,11,12,13-Hexahydro-10-methoxy-9-methyl-1-oxo-9,13-epoxy-1H,9H-diindolo[1,2,3-gh:3',2',1'-lm]pyrrolo[3,4-j][1,7]benzodiazonin-11-yl)methylamino]-3-oxopropyl]-carbamic acid, 1,1-dimethylethyl ester |
| 62996-74-1 | 100% | (9S,10R,11R,13R)-2,3,10,11,12,13-Hexahydro-10-methoxy-9-methyl-11-(methylamino)-9,13-Epoxy-1H,9H-diindolo[1,2,3-gh:3',2',1'-lm]pyrrolo[3,4-j][1,7]benzodiazonin-1-one |

Our invention is furthermore supported by the data disclosed by Weisberg E, Boulton C, Kelly L M, Manley P, Fabbro D, Meyer T, Gilliland D G and Griffin J D in the journal Cancer Cell ("Inhibition of mutant FLT3 receptors in leukemia cells by the small molecule tyrosine kinase inhibitor PKC412"; 2002 Jun.1(5):433-43) hereby incorporated into the present application by reference to this publications.

The invention claimed is:

1. A method for treating a mammal suffering from acute myeloid leukemia comprising orally administering to a mammal in need of such treatment a therapeutically effective amount of up to 150 mg per day of N-[(9S,10R,11R,13R)-2,3,10,11,12,13-hexahydro-10-methoxy-9-methyl-1-oxo-9,13-epoxy-1H,9H-diindolo[1,2,3-gh:3',2',1'-lm]pyrrolo[3,4- j][1,7]benzodiazonin-11-yl]-N-methylbenzamide of the formula (VII):

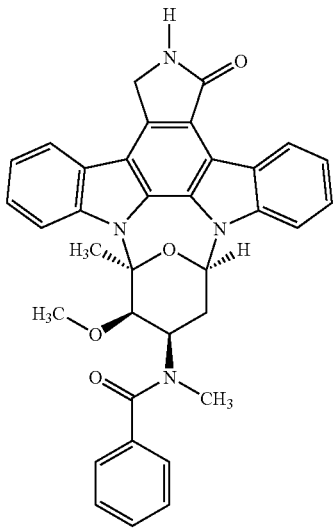

(VII)

or a salt thereof.

2. A method according to claim 1, wherein the acute myeloid leukemia is characterized by deregulated FLT3 receptor tyrosine kinase activity.

3. A method according to claim 1, wherein the compound of formula VII is administered as a microemulsion, soft gel or solid dispersion.

4. A method according to claim 3, wherein the compound of formula VII is administered as a microemulsion.

5. A method according to claim 2, wherein the compound of formula VII is administered as a microemulsion, soft gel or solid dispersion.

6. A method according to claim 5, wherein the compound of formula VII is administered as a microemulsion.

* * * * *